US012758519B2

(12) United States Patent
Van Hoek

(10) Patent No.: US 12,758,519 B2
(45) Date of Patent: Oct. 13, 2026

(54) FELINE FOOD COMPOSITION

(71) Applicant: MARS, INCORPORATED, McLean, VA (US)

(72) Inventor: Ingrid Van Hoek, Aimargues (FR)

(73) Assignee: MARS, INCORPORATED, McLean, VA (US)

( * ) Notice: Subject to any disclaimer, the term of this patent is extended or adjusted under 35 U.S.C. 154(b) by 769 days.

(21) Appl. No.: 17/426,883

(22) PCT Filed: Jan. 30, 2020

(86) PCT No.: PCT/US2020/015808
§ 371 (c)(1),
(2) Date: Jul. 29, 2021

(87) PCT Pub. No.: WO2020/160216
PCT Pub. Date: Aug. 6, 2020

(65) Prior Publication Data

US 2022/0096416 A1 Mar. 31, 2022

(30) Foreign Application Priority Data

Feb. 1, 2019 (EP) .................................... 19305123

(51) Int. Cl.

| | |
|---|---|
| ***A61K 31/202*** | (2006.01) |
| ***A23K 20/147*** | (2016.01) |
| ***A23K 20/158*** | (2016.01) |
| ***A23K 20/163*** | (2016.01) |
| ***A23K 50/42*** | (2016.01) |
| ***A23K 50/45*** | (2016.01) |
| ***A23K 50/48*** | (2016.01) |
| ***A61K 9/00*** | (2006.01) |
| ***A61P 9/04*** | (2006.01) |

(52) U.S. Cl.
CPC .......... *A61K 31/202* (2013.01); *A23K 20/147* (2016.05); *A23K 20/158* (2016.05); *A23K 20/163* (2016.05); *A23K 50/42* (2016.05); *A23K 50/45* (2016.05); *A23K 50/48* (2016.05); *A61K 9/0056* (2013.01); *A61P 9/04* (2018.01)

(58) Field of Classification Search
CPC .. A61K 31/202; A61K 9/0056; A23K 20/147; A23K 20/158; A23K 20/163; A23K 50/42; A23K 50/45; A23K 50/48; A61P 9/04
See application file for complete search history.

(56) References Cited

U.S. PATENT DOCUMENTS

| | | | |
|---|---|---|---|
| 6,203,825 | B1 | 3/2001 | Hodgkins |
| 6,509,178 | B1 | 1/2003 | Tanaka et al. |
| 9,302,016 | B2 | 4/2016 | Sancilio et al. |
| 2008/0233244 | A1 | 9/2008 | Swenson |
| 2008/0293621 | A1 | 11/2008 | Allen et al. |
| 2010/0304003 | A1 | 12/2010 | Friesen et al. |
| 2011/0178005 | A1 | 7/2011 | Yamka et al. |
| 2013/0281533 | A1* | 10/2013 | Yamka .................... A61P 43/00 514/763 |
| 2014/0348929 | A1 | 11/2014 | Sancilio et al. |
| 2014/0348930 | A1 | 11/2014 | Sancilio et al. |
| 2017/0150741 | A1 | 6/2017 | Deuerer |
| 2018/0125101 | A1* | 5/2018 | De Cock ................... A23J 1/12 |
| 2018/0192669 | A1* | 7/2018 | Wilson ................. A23K 20/158 |

FOREIGN PATENT DOCUMENTS

| | | | | |
|---|---|---|---|---|
| CN | 101374421 | A | 2/2009 | |
| CN | 108 497 164 | A | 9/2018 | |
| CN | 109069465 | A | 12/2018 | |
| EP | 2 514 421 | A1 | 10/2012 | |
| FR | 2 847 769 | A1 | 6/2004 | |
| JP | 2014139165 | A | 7/2014 | |
| WO | WO 2004/075653 | A1 | 9/2004 | |
| WO | WO 2010/060874 | A1 | 6/2010 | |
| WO | WO-2014098193 | A1 * | 6/2014 | ............. A23K 10/20 |
| WO | WO 2015/177134 | A1 | 11/2015 | |
| WO | 2018/125029 | A1 | 7/2018 | |
| WO | WO 2018/219877 | A1 | 12/2018 | |

OTHER PUBLICATIONS

Evason, "Chromic Kidney Disease Staging & Nutrition Considerations", cliniciansbrief.com, Mar. 2017. (Year: 2017).*
Watson, "Sodium-Chloride, tripolyphosphate, or nitrite: do dogs really need salts", Mar. 8, 2010. (Year: 2010).*
Becker, "Feline Cardiomyopathy in Cats", Jun. 14, 2015, retrieved from https://www.victoriangardenscattery.com/feline-cardiomyopathy-in-cats-by-dr-karen-becker.html. (Year: 2015).*
Mary, "what is vital wheat gluten and why do I need it—Food52", Nov. 2, 2018; retrieved from https://food52.com/hotline/40396-what-is-vital-wheat-gluten-and-why-do-i-need-it?srsltid=AfmBOorhFL595I-CxPche8Mn06y9ztL505_ciwBMXnl3wiqsKfz2mLZf. (Year: 2018).*
Kainian et al., "Research progress on the relationship between obesity and metabolic and endocrine disorders in dogs and cats," China Academic Journal Electronic Publishing House, China Animal Health, pp. 57-60, Continued from the 11th issue of 2011 (total 153 issues) pet health column (2011) [Machine translation attached].
Takahashi et al., "Dietary fish oil attenuates cardiac hypertrophy in lipotoxic cardiomyopathy due to systemic carnitine deficiency," Cardiovascular Research 68:213-223 (2005).
Abbott et al., "Two-Dimensional Echocardiographic Assessment of the Feline Left Atrium," J Vet Intern Med 20:111-119 (2006).

(Continued)

*Primary Examiner* — Jianfeng Song
(74) *Attorney, Agent, or Firm* — Baker Botts L.L.P.

(57) ABSTRACT

Nutritionally complete feline food compositions comprising EPA/DHA and carbohydrates are disclosed herein. These nutritionally complete feline food compositions can be used in dry or wet food composition. The compositions can be used to for preventing and/or treating cardiac hypertrophy in feline animals, such as cats.

12 Claims, No Drawings

(56) References Cited

OTHER PUBLICATIONS

Extended European Search Report dated Jul. 22, 2019 in Application No. EP19305123.
Fox et al., "Echocardiographic Assessment of Spontaneously Occurring Feline Hypertrophic Cardiomyopathy. An Animal Model of Human Disease," Circulation 92(9):2645-2651 (1995).
Fox et al., "Management of asymptomatic (occult) feline cardiomyopathy: Challenges and realities," Journal of Veterinary Cardiology 17:S150-S158 (2015).
Freeman et al., "A Randomized Study Assessing the Effect of Diet in Cats with Hypertrophic Cardiomyopathy," J Vet Intern Med 28:847-856 (2014).
Freeman et al., "Body size and metabolic differences in Maine Coon cats with and without hypertrophic cardiomyopathy," Journal of Feline Medicine And Surgery, 15(2):74-80 (2013, Accepted 2012).
International Search Report and Written Opinion dated Apr. 23, 2020 in International Application No. PCT/US20/15808.
Riesen et al., "Prevalence of heart disease in symptomatic cats: an overview from 1998 to 2005," Schweizer Archiv fur Tierheilkunde, 149:65-71 (2007).
Rush, "Therapy of Feline Hypertrophic Cardiomyopathy," Advances in Cardiovascular Diagnostics and Therapy, Veterinary Clinics Of North America: Small Animal Practice 28(6):1459-1479 (1998).
Schober et al., "Assessment of Left Atrial Appendage Flow Velocity and its Relation to Spontaneous Echocardiographic Contrast in 89 Cats with Myocardial Disease," J Vet Intern Med 20:120-130 (2006).
Schober et al., "Comparison between invasive hemodynamic measurements and noninvasive assessment of left ventricular diastolic function by use of Doppler echocardiography in healthy anesthetized cats," AJVR 64(1) 93-103 (2003).
Extended European search report dated Oct. 27, 2022 in Application No. EP 20748392.
Singh et al., "Phytochemical Analysis and Characterization of Corn Silk (*Zea mays,* G5417)," Agronomy, 12(4):777 (2022) 13 pgs.

* cited by examiner

FELINE FOOD COMPOSITION

CROSS-REFERENCE TO RELATED APPLICATIONS

This application is a U.S. National Stage Patent Application under 35 U.S.C. § 371 of International Patent Application No. PCT/US2020/015808, filed on Jan. 30, 2020, which claims priority to European patent application no. EP 19305123.2, filed on Feb. 1, 2019, the contents of each of which are incorporated herein by reference in in their entireties, and to each of which priority is claimed.

FIELD

The presently disclosed subject matter relates to the field of nutritionally complete food compositions for preventing and/or treating cats with cardiac hypertrophy.

BACKGROUND

Hypertrophic cardiomyopathy (HCM) is the most common heart disease in cats, and specifically in old cats, and the most common cause of heart failure in this species (Riesen et al, 2007, Schweizer Archiv fur Tierheilkunde; Vol. 149: 65-71 Rush et al., 1998, Veterinary Clinics of North America: Small Animal Practice November 1998; 28:1459-1479). The disease can be characterized by cardiac hypertrophy, which is the abnormal enlargement or thickening of the heart muscle. While the majority of affected cats are assumed to remain free of clinical signs for a long period (known as asymptomatic hypertrophic cardiomyopathy or aHCM), a proportion experiences serious complications such as congestive heart failure and cardiac death (Fox et al., 2018, Circulation 92(9):2645-2651). aHCM is characterized by hypertrophy of the left ventricle with thickening of the interventricular septum and left ventricular wall (LVW), impaired diastolic filling and left atrial enlargement. Moreover, diagnosis is based on echocardiographic measurement of maximum thickness of the interventricular septum or left ventricular wall (Fox, 1995, Circulation 92(9):2645-2651).

Furthermore, it is known that cardiac and renal function have a tight relationship across cat species. It has been observed that the prevalence of aHCM, as well as chronic kidney disease (CKD), increases with the age of the cat. Therefore, adapted treatment of aHCM should also take into account possible CKD, asymptomatic or not.

Treatments proposed in the art can be amenable to interventions or to drug therapies. For instance, EP2514421 discloses the use of torasemide in the treatment of symptoms caused by HCM. Additionally, WO2010060874 discloses the use of phosphodiesterase type III inhibitors and $Ca^{2+}$-sensitizing agents for the treatment of HCM even though the treatment was not satisfactory and was still being tested at the time of the application. Little progress has been made in the treatment of cats with aHCM. Until recently, there was no available data that established a treatment benefit for cats with mild or moderate aHCM (Fox et al., 2015, J. Vet. Cardiology, Vol. 17: S150-S158).

Further research has suggested that diet or certain nutrients can modify phenotypic expression of cardiomyopathy in genetically predisposed individuals (Freeman et al. 2014, J. Vet. Intern. Med., Vol. 28: 847-856). For example, Freeman et al. tested three different cat groups (groups A, B, and C) with two diets such as a dry diet and a wet diet, based on commercially available cat food compositions. For each group, commercially available dry and wet diets were selected that were similar to one another in nutrient profile and ingredients. This test was performed on cats affected with HCM, but which were devoid of clinical signs of heart disease (e.g., aHCM). Group C had a significant decrease in interventricular septal thickness in systole (IVSs), in the left atrial (LA) dimension, and the ratio of the left atrium to the aorta (LA/Ao), as well as a significant decrease in body weight. Nevertheless, group C had a non-statistically significant decrease in inter alia left ventricular free wall thickness in diastole (LVWd) and interventricular septal thickness in diastole (IVSd). In summary, Freeman et al. failed to demonstrate any significant effect of these commercial diets on the treatment of aHCM.

Accordingly, there remains a need for novel food compositions for preventing or treating cardiac hypertrophy.

There remains a need for food compositions which do not affect kidney function in cats with cardiac hypertrophy, particularly asymptomatic hypertrophic cardiomyopathy.

There remains a need for food compositions which do not affect kidney function in cats with cardiac hypertrophy, particularly asymptomatic hypertrophic cardiomyopathy, and no pre-existing chronic kidney disease.

There remains a need for compositions for preventing or treating cardiac hypertrophy, in particular asymptomatic hypertrophic cardiomyopathy, which does not affect kidney function.

The presently disclosed subject matter is aimed at satisfying all or parts of these needs.

SUMMARY

A first aspect of the present disclosure relates to a nutritionally complete feline food composition comprising EPA/DHA and carbohydrates, for its use for preventing and/or treating cardiac hypertrophy, wherein:

- (a) the nutritionally complete food composition consists of a dry food composition comprising:
  - (i) EPA/DHA in an amount of at least about 0.5 g/Mcal; and
  - (ii) Nitrogen-Free Extract (NFE) in an amount of no more than about 60 g/Mcal; or
- (b) the nutritionally complete food composition consists of a wet food composition comprising:
  - (i) EPA/DHA in an amount of at least about 1.0 g/Mcal; and
  - (ii) Nitrogen Free Extract (NFE) in an amount of no more than about 35 g/Mcal.

In some embodiments, said nutritionally complete feline food which is a dry food comprises starch in an amount of no more than about 50 g/Mcal.

In some embodiments, said nutritionally complete feline food which is a wet food comprises starch in an amount of no more than 20 g/Mcal.

In some embodiments, a nutritionally complete feline food composition comprising EPA/DHA and carbohydrates, for use in a method for preventing and/or treating cardiac hypertrophy, comprises:

- (a) the nutritionally complete food composition consists of a dry food composition comprising:
  - (i) EPA/DHA in an amount of at least about 0.5 g/Mcal;
  - (ii) Starch in an amount of no more than about 50 g/Mcal; or
- (b) the nutritionally complete food composition consists of a wet food composition comprising:
  - (i) EPA/DHA in an amount of at least about 1.0 g/Mcal;
  - (ii) Starch in an amount of no more than about 20 g/Mcal.

Further, the above embodiments encompass a nutritionally complete feline food composition comprising EPA/DHA and carbohydrates, for use in a method for preventing and/or treating cardiac hypertrophy, wherein:

(a) the nutritionally complete food composition consists of a dry food composition comprising:
  (i) EPA/DHA in an amount of at least about 0.5 g/Mcal; and
  (ii) Nitrogen-Free Extract (NFE) in an amount of no more than about 60 g/Mcal, said NFE comprising starch in an amount of no more than 50 g/Mcal; or
(b) the nutritionally complete food composition consists of a wet food composition comprising:
  (i) EPA/DHA in an amount of at least about 1.0 g/Mcal; and
  (ii) Nitrogen Free Extract (NFE) in an amount of no more than about 35 g/Mcal, said NFE comprising starch in an amount of no than about 20 g/Mcal.

In some embodiments, said nutritionally complete feline food composition which is a dry food further comprises protein in an amount of at least about 115 g/Mcal.

In some embodiments, said nutritionally complete feline food composition which is a dry food further comprises fat in an amount ranging from about 20 g/Mcal to about 45 g/Mcal.

In some embodiments, said nutritionally complete feline food composition which is a dry food further comprises arginine in an amount of no more than about 9 g/Mcal.

In some embodiments, said nutritionally complete feline food which is a wet food comprises starch in an amount of no more than about 20 g/Mcal.

In some embodiments, said nutritionally complete feline food composition which is a wet food further comprises protein in an amount of at least about 117 g/Mcal.

In some embodiments, said nutritionally complete feline food composition which is a wet food further comprises fat in an amount ranging from about 20 g/Mcal to about 45 g/Mcal.

In some embodiments, said nutritionally complete feline food composition which is a wet food further comprises arginine in an amount of no more than about 9 g/Mcal.

In some embodiments, said nutritionally complete feline food composition is used for decreasing thickening of cardiac wall.

In some embodiments, said nutritionally complete feline food composition is used for decreasing blood concentration of Insulin like growth factor I (IGF-I).

In some embodiments, said nutritionally complete feline food composition is used for decreasing blood concentration of cardiac Troponin I (cTnI).

In some embodiments, said nutritionally complete feline food composition is used for preventing and/or treating cats with a cardiac hypertrophy.

In some embodiments, said nutritionally complete feline food composition is used for preventing and/or treating cats with a cardiac hypertrophy, wherein said cats are affected with asymptomatic hypertrophic cardiomyopathy and wherein said cats are affected with asymptomatic hypertrophic cardiomyopathy in the absence of LA remodeling.

In some embodiments, a nutritionally complete feline food composition of the present disclosure is used for preventing and/or treating cats, wherein said composition causes no significant change in the feline body weight.

A second aspect of the present disclosure further relates to a nutritionally complete feline food composition as defined above and throughout the present specification.

A third aspect to the present disclosure further relates to a method for treating cardiac hypertrophy in a cat affected with asymptomatic hypertrophic cardiomyopathy comprising at least a step of feeding the cat with a nutritionally complete feline food composition.

Another aspect to the present disclosure further relates to a method for treating cardiac hypertrophy in a cat affected with asymptomatic hypertrophic cardiomyopathy comprising at least a step of making a feeding recommendation that includes a nutritionally complete feline food composition.

The present disclosure also relates to a nutritionally complete feline food composition comprising EPA/DHA, carbohydrates and protein, for use in a method for preventing and/or treating chronic kidney disease (CKD), wherein (a) the nutritionally complete feline food composition consists of a dry food composition comprising:
  (i) EPA/DHA in an amount of at least about 0.5 g/Mcal;
  (ii) Nitrogen-Free Extract (NFE) in an amount of no more than about 60 g/Mcal; and
  (iii) protein in an amount of at least about 115 g/Mcal; or
(b) the nutritionally complete feline food composition consists of a wet food composition comprising:
  (i) EPA/DHA in an amount of at least about 1.0 g/Mcal;
  (ii) Nitrogen Free Extract (NFE) in an amount of no more than about 35 g/Mcal; and
  (iii) protein in an amount of at least about 117 g/Mcal.

In some embodiments the nutritionally complete feline food composition consists of the nutritionally complete feline food composition of the present disclosure.

The present disclosure also relates to a nutritionally complete feline food composition, as described above in the present disclosure, comprising EPA/DHA, carbohydrates and protein, for use in a method for preventing and/or treating chronic kidney disease in cats affected with aHCM, specifically in old cats affected with aHCM.

The cats considered can have, or not, a chronic kidney disease.

In some embodiments, the present disclosure relates to a nutritionally complete feline food composition comprising EPA/DHA in an amount of at least about 0.5 g/Mcal and Nitrogen Free Extract in an amount of no more than about 60 g/Mcal, wherein the composition is a dry food composition.

In certain particular embodiments, the dry food composition comprises starch in an amount of no more than about 50 g/Mcal.

In certain particular embodiments, the dry food composition comprises protein in an amount of at least about 115 g/Mcal.

In certain particular embodiments, the dry food composition comprises fat in an amount of from about 20 g/Mcal to about 45 g/Mcal.

In certain particular embodiments, the dry food composition comprises arginine in an amount of no more than about 9 g/Mcal.

In some embodiments, the present disclosure relates to a nutritionally complete feline food composition comprising EPA/DHA in an amount of at least about 1.0 g/Mcal and Nitrogen Free Extract in an amount of no more than about 35 g/Mcal, wherein the composition is a wet food composition.

In certain particular embodiments, the wet food composition comprises starch in an amount of no more than about 20 g/Mcal.

In certain particular embodiments, the wet food composition comprises protein in an amount of at least about 117 g/Mcal.

In certain particular embodiments, the wet food composition comprises fat in an amount of from about 20 g/Mcal to about 45 g/Mcal.

In certain particular embodiments, the wet food composition comprises arginine in an amount of no more than about 9 g/Mcal.

In certain embodiments, the present disclosure provides for a method for preventing and/or treating cardiac hypertrophy in a feline in need thereof, the method comprising providing the feline a nutritionally complete feline food composition.

In certain particular embodiments, the feline is a cat.

In certain particular embodiments, the cat is affected with asymptomatic hypertrophic cardiomyopathy.

DETAILED DESCRIPTION

The present disclosure provides nutritional food products for treating and/or preventing cardiac hypertrophy. In certain embodiments, the nutritional food products disclosed herein can be used for treating and/or preventing asymptomatic hypertrophic cardiomyopathy (aHCM), in feline animals, especially in cats. The nutritional product disclosed herein is capable of acting on the progression of thickening of the cardiac wall, limiting spontaneous heart disease while maintaining a good nutritional status (body weight and Body Condition Score (BCS)) In certain embodiments, the nutritional product provided herein is capable of maintaining proper kidney function in cats, specifically, older cats. In certain embodiments, the nutritional product is capable of not affecting kidney function in a cat having aHCM with or without chronic kidney disease (CKD).

The presently disclosed subject matter has been achieved by providing a nutritionally complete feline food composition, available in wet or in dry form, comprising a high amount of EPA/DHA and a moderate amount of Nitrogen Free Extract. As it is shown in the examples herein, such a nutritionally complete feline food composition, when provided to cats with cardiac hypertrophy, particularly cats affected with aHCM, is well tolerated and significantly decreases thickening of the cardiac wall, especially of interventricular septum (IVS) and left ventricular wall (LVW).

As shown in the examples herein, the nutritionally complete feline food composition of the present disclosure causes a reduction in the thickness of the cardiac wall in feline animals undergoing a cardiac hypertrophy. In certain embodiments, as is shown herein, the nutritionally complete feline food composition causes a reduction in the thickness of the interventricular septum as well as of the left ventricular wall in felines that are subject to cardiac hypertrophy, includes feline animals at an early stage of an affection involving cardiac hypertrophy. Particularly, a nutritionally complete diet as disclosed herein has been shown to reduce cardiac hypertrophy in feline animals at an early stage of aHCM, i.e., at a stage of an HCM which is asymptomatic.

The unexpected beneficial effects of a nutritionally complete food composition as disclosed herein are also illustrated by (i) a regulation of the heart rate, (ii) a reduction of the level of circulating troponin-I, (iii) a reduction in the peak of insulin without inducing changes in the mean level of insulin, (iv) no detrimental effects on kidney function, as well as (v) a reduction in the level of circulating IGF-1, which beneficial effects denote a reversion of the cardiac muscle alterations caused by cardiac hypertrophy, i.e., HCM, and especially aHCM.

In certain embodiments, as shown in the examples, the nutritionally complete feline food composition of the present disclosure is acting at a very early stage of a cardiac hypertrophy, including at a very early stage of a HCM, as it is illustrated by the induction of the various above-described beneficial effects in feline animals subject to an increase in the thickness of the cardiac wall, especially an increase in the thickness of the interventricular septum and of the left ventricular wall, in the absence of a remodeling of the left atrium (LA).

As provided in the Examples below, it was surprisingly and advantageously found that, although food compositions comprising a high amount of protein are generally associated with worse outcome of CKD, the nutritionally complete food compositions of the present disclosure do not affect renal function in cats with aHCM.

The present disclosure also relates to a nutritionally complete feline food composition comprising a high amount of EPA/DHA and a moderate amount of Nitrogen Free Extract. Such a composition is useful for treating or preventing cardiac hypertrophy in an animal, and more particularly an animal affected with aHCM. In certain embodiments the animal is a feline. In certain embodiments, the animal is a cat. The nutritionally complete food composition of the present disclosure can also be used in a method for treating a feline with cardiac hypertrophy, including a feline affected with aHCM. In certain embodiments, the nutritionally complete food composition of the present disclosure is a dry feline food composition. In certain embodiments, the nutritionally complete food product of the present disclosure is a dry cat food composition. In certain other embodiments, the nutritionally complete feline food composition of the present disclosure is a wet food composition. In certain embodiments, the nutritionally complete food composition of the present disclosure is a wet cat food composition.

In certain embodiments, the present disclosure relates to a nutritionally complete feline food composition comprising EPA/DHA in an amount of at least about 0.5 g/Mcal and Nitrogen Free Extract (NFE) in an amount of no more than about 60 g/Mcal, for its use for preventing and/or treating cardiac hypertrophy.

In certain embodiments, the present disclosure relates to a dry nutritionally complete feline food composition comprising EPA/DHA and carbohydrates, and uses thereof for prevention and/or treatment of cardiac hypertrophy, wherein EPA/DHA is present in an amount of at least about 0.5 g/Mcal and Nitrogen Free Extract is present in an amount of no more than about 60 g/Mcal.

In certain embodiments, the present disclosure relates to a wet nutritionally complete feline food composition comprising EPA/DHA and carbohydrates, and uses thereof for prevention and/or treatment of cardiac hypertrophy, wherein EPA/DHA is present in an amount of at least about 1.0 g/Mcal and Nitrogen Free Extract in an amount of no more than about 35 g/Mcal.

In certain embodiments, the present disclosure relates to a nutritionally complete feline food composition comprising EPA/DHA and carbohydrates, and uses thereof for prevention and/or treatment of cardiac hypertrophy, wherein the nutritionally complete food composition comprises a dry food composition comprising EPA/DHA in an amount of at least about 0.5 g/Mcal and Nitrogen Free Extract in an amount of no more than about 60 g/Mcal, or the nutritionally complete feline food composition comprises a wet food composition comprising EPA/DHA in an amount of at least about 1.0 g/Mcal and Nitrogen Free Extract in an amount of no more than about 35 g/Mcal.

Definitions

The terms used in this specification generally have their ordinary meanings in the art, within the context of this disclosure and in the specific context where each term is used. Certain terms are discussed below, or elsewhere in the specification, to provide additional guidance in describing the compositions and methods of the disclosure and how to make and use them.

As used in the specification and the appended claims, the singular forms "a," "an" and "the" include plural referents unless the context clearly dictates otherwise. Thus, for example, reference to "a compound" includes mixtures of compounds.

The term "about" or "approximately", as used herein, means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 10%, more preferably up to 5%, and more preferably still up to 1% of a given value.

As used herein, the terms "animal" or "pet" can be used, for example, to refer to domestic or wild animals. In certain embodiments, the terms can refer to cats or felines.

As used herein, the terms "comprises," "comprising," or any other variation thereof, are intended to cover a non-exclusive inclusion, such that a process, method, article, or apparatus that comprises a list of elements does not include only those elements but can include other elements not expressly listed or inherent to such process, method, article, or apparatus.

In the detailed description herein, references to "embodiment," "an embodiment," "one embodiment," "in various embodiments," etc., indicate that the embodiment(s) described can include a particular feature, structure, or characteristic, but every embodiment might not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

As used herein, the term "EPA/DHA" designates a fatty acid or a mixture of fatty acids consisting of (i) only eicosapentaenoic acid (EPA), (ii) only docosahexaenoic acid (DHA) or (iii) a combination of eicosapentaenoic acid and docosahexaenoic acid (EPA+DHA).

As used herein, an amount of a component expressed as weight/Mcal refers to a weight amount of the said component by unit of Metabolizable Energy (ME) of the total food composition. Metabolizable Energy is conventionally determinable according to standard methods, and especially according to the European Standard EN 16967 (ICS.65.120) dated of July 2017.

As used herein, the terms "food composition" or "diet" refer to a material containing proteins, carbohydrates and/or fats, which is used in the body of an organism to sustain growth, repair and vital processes and to furnish energy. Foods can also contain supplementary substances or additives, for example, minerals, vitamins and condiments (See Merriam-Webster's Collegiate Dictionary, 10th Edition, 1993). In a particular embodiment, a feline food composition according to the present disclosure consists of a nutritionally complete food composition that provides the complete and balanced nutritional requirement to feline animals, and especially cats. Thus, a food composition as described herein is a complete feline food; e.g., a complete cat food, that is a nutritionally adequate feed with which the said feline animal, e.g., the said cat, can be fed as the sole ration and is capable of sustaining life without additional food (except water). Further, said nutritionally complete feline food composition causes no significant change in the feline, i.e., cat, body weight and/or also in the Body Condition Score (BCS). The food composition can contain a carrier, a diluent, or an excipient. Depending on the intended use, the carrier, diluent, or excipient can be chosen to be suitable for animal use, especially for feline animals use such as cats.

Illustratively, a nutritionally complete food composition as described herein can include, but it is not limited to, cereals and vegetable protein extracts, fibers, oils and fats, proteins, chicory pulps, yeasts and parts thereof, minerals, Vitamins, preservatives, antioxidants, water, arginine, sodium.

As used herein, the terms "dry food", "wet food" and "semi-moist food" designate a nutritionally complete feline food product encompassing any product which a feline animal consumes in its diet. In certain embodiments, the feline food product is a cooked product. It can incorporate meat or animal derived material (such as beef, chicken, turkey, lamb, fish, blood plasma, marrow bone etc. or one or more thereof). The product alternatively can be meat free (and in certain embodiments can include a meat substitute such as soya, maize gluten or a soya product) in order to provide a protein source.

As used herein, the term "feline" encompasses animals, including pet animals, including older pet animals, selected in the group comprising cheetah, puma, jaguar, leopard, lion, lynx, liger, tiger, panther, bobcat, ocelot, smilodon, caracal, serval and cats. As used herein, cats encompass wild cats and domestic cats. In particular embodiments, the cats are domestic cats. In more particular embodiments, the cats are old cats.

As used herein, a "cardiac hypertrophy" relates to the abnormal enlargement, or thickening of the heart muscle, resulting from increases in cardiomyocyte size and changes in other heart muscle components, such as extracellular matrix, due to chronic and increased stress on the heart. Cardiac hypertrophy encompasses HCM, which is characterized by hypertrophy of the left ventricle associated with a thickening of the interventricular septum and left ventricular wall. If the hypertrophy is mild and focal, the cat can remain symptom-free for a long time (aHCM). However, if the hypertrophy is severe, the ventricle will have a hard time distending, with increased left-sided heart filling pressure, and dilatation of the left atrium (LA-remodeling in response to the increased pressures). HCM in cats can be secondary to pressure overload due to systemic hypertension or outflow obstruction, as well as secondary to hormonal stimulation as in hyperthyroidism and hypersomatotropism/acromegaly.

According to the present disclosure, HCM encompasses aHCM.

As used herein, "chronic kidney disease" (CKD) relates to a type of kidney disease in which there is gradual loss of kidney function over a period of months to years. At the outset, there are generally no symptoms. Complications can include an increased risk of heart diseases.

As used herein, a significant change or difference or decrease or increase is a reproductible (p-value<0.05), i.e., consistently observed, change or difference or decrease or increase in the parameter tested, including for example, but not limited to parameters tested in Table 8). The measure of a p-value is known to the skilled person depending on the available values and experimental conditions.

As used herein, a no significant change or difference or decrease is a non-reproducible (p-value>0.05), i.e., consistently observed, change or difference or decrease in the parameters tested, including, for example, but not limited to parameters tested in Table 8).

As used herein the term "providing" refers to selling, supplying, administering, or feeding.

As used herein, "to not affect" with regard to a given physiological function intends to mean that the parameter(s) defining this physiological and its status is/are not significantly modified overtime, with or without any adjunct treatment(s).

As used herein, the term "weight percent" or "wt %" or "by weight" is meant to refer to either (i) the quantity by weight of a constituent/component in a composition as a percentage of the total weight of the composition; or (ii) the quantity by weight of a constituent/component in the material as a percentage of the weight of the final material or product.

Food Composition

The food compositions of the present disclosure can comprise a wide variety of components. Non-limiting examples of components that can be incorporated in the food compositions of the present disclosure are listed below.

EPA/DHA

In certain embodiments, the composition can include eicosapentaenoic acid and/or docosahexaenoic acid. As used herein, the term "EPA/DHA" designates a fatty acid or a mixture of fatty acids consisting of (i) only eicosapentaenoic acid (EPA), (ii) only docosahexaenoic acid (DHA) or (iii) a combination of eicosapentaenoic acid and docosahexaenoic acid (EPA+DHA). Thus, an amount of "EPA/DHA" can mean any of the following: (i) an amount of EPA, in the absence of DHA, (ii) an amount of DHA, in the absence of EPA, or (iii) an amount of a combination of EPA and DHA.

Accordingly, the nutritionally complete feline food composition as disclosed herein comprises EPA, or DHA or a combination of EPA and DHA, at a specified EPA/DHA weight amount by unit of Metabolizable energy of the total food composition.

In certain embodiments of the present disclosure, where a nutritionally complete feline food comprises "X g/Mcal" of EPA/DHA, the feline food can comprise X g/Mcal of EPA and is devoid of DHA. According to these embodiments, X g/Mcal EPA/DHA equates to X mg/Mcal EPA, without DHA.

In certain other embodiments of the present disclosure, a nutritionally complete feline food comprises "X g/Mcal" of EPA/DHA, the feline food can comprise X g/Mcal of DHA and is devoid of EPA. According to these other embodiments, X mg/Mcal EPA/DHA equates to X mg/Mcal DHA, without EPA.

In certain embodiments of the present disclosure, a nutritionally complete feline food comprises "X g/Mcal" of EPA/DHA, the feline food can comprise X g/Mcal of a combination of EPA and DHA. According to these embodiments, EPA and DHA are both present in the composition. Additionally, in these embodiments, there is no specific requirement regarding the respective amount of EPA and DHA present in the EPA/DHA combination. For example, and not by the way of limitation, the weight/energy ratio of EPA to DHA can range from about 0.0001 to about 1000.

The properties of mixtures containing EPA/DHA, have been described in the past in several documents, for example: in the treatment of thromboses, in hypercholesterolemia, in myocardial ischemia (WO87/03899), in the prevention of arteriosclerosis, in cerebral infarction, in hyperlipemiae, in cardiac infarction (EP0228314), in the prophylaxis of atherosclerosis, as antithrombotic, as antihypertensive (JP62091188), in thrombotic pathologies, in platelet agglutination, in self-immune syndromes, in acute and chronic inflammations, in atherosclerosis, cardiac infarction, in venous thromboses, in hyperlipemic states, in hypertension, in lesions and occlusions originated by vasomotor spasms, in diabetes (WO87/02247), in the prevention of the side effects of non-steroid anti-inflammatory agents (EP0195570), in the prophylaxis and management of diabetes complications (JP60-248610), in hypercholesterolemiae, in hyper triglyceridemiae (DE3438630), as anticoagulants, in hypercholesterolemiae (BE899184).

In certain embodiments, the EPA/DHA is present in the dry food composition of the present disclosure in an amount of at least about 0.5 g/Mcal. In certain embodiments, the EPA/DHA is present in the wet food composition of the present disclosure in an amount of at least about 0.5 g/Mcal, at least about 1.0 g/Mcal, at least about 1.5 g/Mcal, at least about 2.0 g/Mcal, at least about 2.5 g/Mcal, at least about 3.0 g/Mcal, at least about 3.5 g/Mcal, at least about 4.0 g/Mcal, at least about 4.5 g/Mcal, at least about 5.0 g/Mcal, at least about 5.5 g/Mcal, at least about 6.0 g/Mcal, at least about 6.5 g/Mcal, at least about 7.0 g/Mcal, at least about 7.5 g/Mcal, at least about 8.0 g/Mcal, at least about 8.5 g/Mcal, at least about 9.0 g/Mcal, at least about 9.5 g/Mcal, or least about 10 g/Mcal.

In certain embodiments, the EPA/DHA is present in a wet food composition in an amount of at least about 1.0 g/Mcal. In certain embodiments, the EPA/DHA is present in a wet food composition in an amount of at least about 1.0 g/Mcal, at least about 1.5 g/Mcal, at least about 2.0 g/Mcal, at least about 2.5 g/Mcal, at least about 3.0 g/Mcal, at least about 3.5 g/Mcal, at least about 4.0 g/Mcal, at least about 4.5 g/Mcal, at least about 5.0 g/Mcal, at least about 5.5 g/Mcal, at least about 6.0 g/Mcal, at least about 6.5 g/Mcal, at least about 7.0 g/Mcal, at least about 7.5 g/Mcal, at least about 8.0 g/Mcal, at least about 8.5 g/Mcal, at least about 9.0 g/Mcal, at least about 9.5 g/Mcal, or at least about 10 m/Mcal.

Nitrogen Free Extract (NFE)

In certain embodiments, the composition can include nitrogen free extract (NFE). As used herein, and as known in the art, the NFE comprises soluble carbohydrate fraction. The nutritionally complete feline food compositions disclosed herein comprise NFE.

NFE can encompass a wide variety of soluble polysaccharides, starch, gums, mucilages and pectin, if present in the food compositions of the presently disclosed subject matter. As conventionally known in the art, NFE does not comprise the insoluble carbohydrate fraction comprised in the crude fiber material that can, in some embodiments, be present in the said food composition.

Typically, the amount of NFE in a food composition is determined by subtracting the content of each of the other components (protein, fat, crude fiber, ash) from the whole dry matter of the said food composition.

In certain embodiments, where the qualitative and quantitative features of a food composition are expressed as the energy density (e.g., the metabolizable energy density in g/Mcal), the NFE content is determined by subtracting the energy value of each of the other components (protein, fat, crude fiber, ash) from the energy value of the whole food composition.

In certain embodiments, where the qualitative and quantitative features of a food composition are expressed as a weight percentage (e.g., a weight percentage based on the total weight of dry matter of the said composition), the NFE content is determined by subtracting the weight percentage of the other components (protein, fat, crude fiber, ash) from the total weight of the said food composition.

In certain embodiments, the NFE is present in the dry food composition of the present disclosure in an amount of no more than about 60 g/Mcal. In certain embodiments, the NFE is present in the dry food composition of the present disclosure in an amount of no more than about 60 g/Mcal, no more than about 55 g/Mcal, no more than about 50 g/Mcal, no more than about 45 g/Mcal, no more than about 40 g/Mcal, no more than about 35 g/Mcal, no more than about 30 g/Mcal, no more than about 25 g/Mcal, no more than about 20 g/Mcal, no more than about 15 g/Mcal, or no more than about 10 g/Mcal.

In certain embodiments, the NFE is present in the wet food composition of the present disclosure in an amount of no more than about 35 g/Mcal, no more than about 30 g/Mcal, no more than about 25 g/Mcal, no more than about 20 g/Mcal, no more than about 15 g/Mcal, or no more than about 10 g/Mcal.

Carbohydrates

In certain embodiments, the composition can include carbohydrates. As used herein, the term "carbohydrates" designates a mixture of polysaccharides and sugars that are metabolized for energy when hydrolyzed in the body. The carbohydrate content in the food composition can be determined by any number of methods known by those of skilled in the art. Carbohydrates can be supplied under the form of any of a variety of carbohydrate sources known by those skilled in the art, including starch (any kinds, corn, wheat, barley, etc.) beet pulp (which contain a bit of sugars), and psyllium.

Starches

An important source of the Nitrogen Free Extract that is comprised in a nutritionally complete feline food composition disclosed herein consists of starch. A person skilled in the art will appreciate a wide variety of starches are suitable for use in compositions of the present disclosure.

In certain embodiments, the term "starch" as used herein refers to a polysaccharide that is composed of amylose and amylopectin. Starch occurs in many plant tissues as granules, usually between 1 and 100 μm in diameter, depending upon the plant source. Chemically, starches are polysaccharides composed of α-D-glucopyranosyl units linked together with α-D(1-4) and/or α-D(1-6) linkages and are comprised of two molecular types: amylose, the straight chain polyglucan comprised of approximately 1000, α-D(1-4) linked glucoses; and amylopectin, the branched glucan, comprised of approximately 4000 glucose unite with branches occurring as α-D(1-6) linkages.

As used herein, starch encompasses the various crystalline structures of A-type, B-type and C-type starches, which contain different proportions of amylopectin. A-type starches are found mainly in cereals, while B-type starches are found mainly in tubers and amylose-rich starches. C-type starch consists of a mixture of both A and B forms and is found mainly in legumes.

In general, digestible starches are broken down (hydrolyzed) by the enzymes a-amylases, glucoamylase and sucrose-iso-maltase in the small intestine to yield free glucose that is then absorbed.

Starch comprised in a nutritionally complete feline food disclosed herein can be any starch suitable for dietary purpose.

Indeed, the native starch comprised in the starting materials used for preparing a nutritionally complete feline food composition as described herein is susceptible to undergo changes during the manufacture process. However, it is shown herein that, irrespective of the conditions used for the manufacturing method (e.g., dry, wet or semi-moist), and thus irrespective of the physico-chemical changes possibly undergone by the starch during process, the resulting final feline food product fully exert its beneficial effects against cardiomyopathy, including hypertrophic cardiomyopathy (HCM), and especially against asymptomatic HCM.

The specified amount of starch comprised in a nutritionally complete feline food composition described in the present disclosure consists of the amount of starch that is contained in the total amount of the raw materials which are provided for producing the said food composition.

However, the amount of starch comprised in the nutritionally complete feline food composition disclosed herein equates the total amount of starch comprised in the starting materials used for preparing the said feline food composition.

If not already known by advance, the starch content of the starting materials used for preparing a nutritionally complete feline food composition described herein can be determined according to conventional techniques known in the art, and especially according to the known polarimetric method, such as according to NF EN ISO 10520.

In certain embodiments where the starting materials can comprise also modified starch or pre-gelatinized starch, the starch content can also be determined according to NF EN ISO 15914.

The present disclosure provides a nutritionally complete feline food composition comprising EPA/DHA and Nitrogen Free Extract. The nutritionally complete feline food composition disclosed herein comprises a high amount of EPA/DHA and a moderate amount of Nitrogen Free Extract. The nutritionally complete feline food composition can comprise a wet food product, a semi-wet food product, or of a dry food product. It is shown herein that a dry or wet food composition comprising a high amount of EPA/DHA with a moderate amount of Nitrogen Free Extract decreases the thickening of the cardiac wall and particularly the thickening of the interventricular septum (IVS), and more particularly the thickening of the interventricular septum as measured at the end of diastole (IVSd) and the left ventricular wall (LVW) and more particularly the left ventricular wall as measured at the end of diastole (LVWd) in feline animals with a cardiac hypertrophy, and particularly cats affected with HCM or aHCM).

Proteins

In certain embodiments, the nutritionally complete feline food composition of the present disclosure can comprise a high amount of protein. The protein content of the composition according to the present disclosure can be sufficiently high so as to ensure maintenance of lean body mass. A nutritionally complete feline food composition according to the present disclosure can contain one or more distinct source(s) of proteins. Generally, a nutritionally complete feline food composition as described herein comprises a plurality of proteins that are contained in a protein source(s) which can be used in the manufacture process. In certain embodiments, a protein comprised in a nutritionally complete feline food composition is in a native form. In certain other embodiments a protein can be present in an at least partially hydrolysed form, including a protein which is almost completely hydrolyzed. In certain embodiments, a nutritionally complete feline food composition according to the present disclosure can incorporate proteins in the form of meat or animal derived material such as beef, chicken, turkey, lamb, fish, blood plasma, bone marrow, etc., or one or more thereof). In certain other embodiments, a nutritionally complete feline food composition as described herein can be meat-free and can comprise a meat substitute protein source such as soya, maize gluten, or any other protein-containing soya product in order to provide a protein source. In certain embodiments, a nutritionally complete feline food composition of the present disclosure can comprise additional protein sources such as soya protein concentrate, milk proteins, gluten, etc.

Fats

In certain embodiments, the nutritionally complete feline food composition according to the present disclosure can further contain a nutritionally appropriate amount of fat.

The expression “fat” as used in the present specification comprises any food-acceptable fat(s) and/or oil (s) irrespective of their consistency at room temperature, i.e., irrespective whether said “fat” is present in essentially fluid form or in essentially solid form. The composition according to the present disclosure can comprise fat of animal and/or vegetable origin. Fat can be supplied by any of a variety of sources known by those skilled in the art. Plant fat sources include, without limitation, wheat, sunflower, safflower, rapeseed, olive, borage, flaxseed, peanuts, blackcurrant seed, cottonseed, wheat, germ, corn germ, as well as oils derived from these and other plant fat sources. Animal sources include, for example and without limitation, chicken fat, turkey fat, beef fat, duck fat, pork fat, lamb fat, etc., fish oil or any meat, meat by-products, seafood, dairy, eggs, etc. Fat content of foods can be determined by any number of methods known by those of skill in the art.

Arginine

In certain embodiments of the present disclosure, the nutritionally complete feline food composition according to the present can further comprise arginine in amounts sufficient for maintaining feline health. Arginine is an essential nutrient for cats. Specifically, arginine provides a unique example of a nutrient so critical that one meal without dietary arginine can result in death. On the other hand, a high level of arginine can be catabolized in nitric oxide (NO) and can cause inflammation. As it is readily understood, arginine is commonly contained in the protein comprised in the complete feline food. Thus, in most embodiments, arginine is not added as a specific supplement for fulfilling the arginine amount requirement of a nutritionally complete feline food as disclosed herein.

Sodium

In certain embodiments of the present disclosure, the nutritionally complete feline food composition comprises sodium ($Na^+$). In particular embodiments, a low amount of sodium is used. Sodium is an essential mineral for life. Found in the blood and in the fluid that surrounds cells, sodium maintains the cellular environment and prevents cells from swelling or dehydrating. Sodium is also important for maintaining proper nerve and muscle cell function. Accordingly, a specific sodium amount in cat foods is appropriate for healthy cats. The sodium content in feline food composition can be balanced in proper proportions with energy, other minerals, vitamins, fats, proteins, and carbohydrates. Sodium sources include, for example and without limitation, meat, poultry, fish, and eggs etc. Sodium sources also can be in the form of table salt.

Fibers

In certain embodiments of the present disclosure, the nutritionally complete feline food composition comprises one or more dietary fibers.

As used herein, the term “fibers” is similar to “dietary fibers” and shall be interpreted for the purpose of the present disclosure as Total Fibers, meaning that it includes soluble fibers and insoluble fibers. Soluble fiber can be defined as being resistant to digestion and absorption in the small intestine and undergo complete or partial fermentation in the large intestine by opposition to insoluble fiber that can be defined as non-starch polysaccharides that are resistant to digestion and absorption in the small intestine, and resistant to fermentation in the large intestine. Soluble fibers are considered as having a prebiotic effect by providing short chain fatty acids as a source of energy to colonocytes. Insoluble fibers are considered as useful for transit and ballast effect.

Non-limiting examples of fibers include a first group comprising beet pulp, guar gum, chicory root, psyllium, pectin, blueberry, cranberry, squash, apples, oats, beans, citrus, barley, peas, or combinations thereof, and a second group comprising cellulose, whole wheat products, wheat oat, corn bran, flax seed, grapes, celery, green beans, cauliflower, potato skins, fruit skins, vegetable skins, peanut hulls soy fiber, or combinations thereof. In a particular embodiment, the nutritionally complete feline food composition of the present disclosure comprises chicory pulp or cellulose.

In certain non-limiting embodiments, a nutritionally complete feline food composition, as described herein, can comprise fibers in an amount of at least about 0.5% by weight, based on the total weight of dry matter.

The weight percentages expressed herein are by weight of the total weight of the dry matter food composition unless expressed otherwise.

Other Ingredients

In certain embodiments, the nutritionally complete feline food as described herein can also contain supplementary substances or additives, for example, minerals, vitamins and condiments (See Merriam-Webster's Collegiate Dictionary, 10th Edition, 1993).

In certain embodiments, the nutritionally complete feline food as described herein can include ash. Ash can include minerals, such as calcium, phosphorus, sodium, chloride, potassium, magnesium, or combinations thereof. The ash content, if specified as a result of an analytical measure of a feline food composition described herein, is a measure of the total amount of minerals comprised therein. The mineral content is a measure of the amount of specific inorganic components comprised therein, which includes calcium (Ca), sodium (Na), potassium (K) and chlorine (Cl).

As it shall be readily understood, every embodiment of a nutritionally complete feline food composition encompassed by the present disclosure comprises a variety of ingredients, each comprised in the said composition at a given weight percentage, as compared to the total weight of dry matter of the nutritionally complete feline food composition.

In certain embodiments, a nutritionally complete feline food composition as disclosed herein comprises protein, carbohydrate, fat, one more sources of EPA/DHA, optionally fibers, and optionally one or more further ingredients such as vitamins, minerals, etc., the sum of the weight of each of the ingredients comprised therein amounting to 100% by weight, based on the total weight of dry matter of the said feline food composition.

Dry Food Composition

In certain embodiments, a nutritionally complete feline food composition as described herein comprises a dry food composition comprising EPA/DHA in an amount of at least about 0.5 g/Mcal and (ii) Nitrogen Free Extract in an amount of no more than about 60 g/Mcal.

In certain embodiments, the nutritionally complete feline dry food composition comprises EPA/DHA in an amount of about 0.6 g/Mcal.

Without wishing to be bound by any particular theory, it is understood that very high amounts of EPA/DHA, e.g., amounts of EPA/DHA higher than about 10 g/Mcal can cause potential adverse effects, which can include hemostatic alterations due to anti-aggregatory effects on platelets, vitamin E deficiency, lipid peroxidation and mild diarrhea.

In certain embodiments, the amount of Nitrogen Free Extract present in a nutritionally complete feline dry food composition according to the present disclosure is at least about 1 g/Mcal.

Starch is one of the sources of the Nitrogen Free Extract comprised in a nutritionally complete feline dry food composition according to the present disclosure.

In certain embodiments, a nutritionally complete feline dry food composition according to the present disclosure comprises starch in an amount of no more than about 50 g/Mcal.

In certain embodiments, starch is provided from a cereal source. Certain non-limiting embodiments of sources of starch encompass staple foods like potatoes, wheat, maize (corn), rice, and cassava.

In certain embodiments, the nutritionally complete feline dry food composition comprises protein in an amount of at least about 115 g/Mcal.

In certain embodiments, the nutritionally complete feline dry food composition comprises protein in an amount of about 125 g/Mcal.

In certain embodiments, the nutritionally complete feline dry food composition comprises fat in an amount ranging from about 20 g/Mcal to about 45 g/Mcal.

In certain embodiments, the nutritionally complete feline dry food composition of the present disclosure comprises fat in an amount ranging from about 30 g/Mcal to about 40 g/Mcal, or from about 30 g/Mcal to about 35 g/Mcal.

In certain non-limiting embodiments, the dry food composition comprises fat in an amount of about 35 g/Mcal.

In certain embodiments, the nutritionally complete feline dry food composition comprises arginine in an amount of no more than about 9 g/Mcal.

In certain embodiments, the nutritionally complete feline dry food composition comprises arginine in an amount of about 8 g/Mcal.

In certain embodiments, the nutritionally complete feline dry food composition comprises sodium ($Na^{t}$) in an amount of no more than about 0.7 g/Mcal. In certain embodiments, the nutritionally complete feline dry food composition comprises sodium in an amount of about 0.68 g/Mcal.

In certain embodiments, the amount of sodium in the nutritionally complete feline dry food composition is at least about 0.19 g/Mcal.

In certain embodiments, the nutritionally complete feline dry food composition comprises one or more components selected from the group consisting of barley, psyllium and its derivatives, starch and native wheat gluten.

According to an illustrative embodiment, the nutritionally complete feline dry food composition comprises one or more components selected from the group consisting of (i) barley in an amount of at least about 45 g/Mcal, (ii) psyllium and its derivatives in an amount of at least about 3.50 g/Mcal, (iii) starch in an amount of no more than about 40 g/Mcal, (iv) native wheat gluten in an amount of at least about 50 g/Mcal, and (v) combinations thereof.

Barley comes in two varieties, distinguished by the number of rows of flowers on its flower spike. Two-row barley has central florets that produce kernels and lateral florets that are normally sterile. Whereas six-row barley has a higher protein content and is more suited for animal feed, two-row barley has a higher sugar content and is thus more commonly used for malt production.

As used herein, a "psyllium and its derivatives" refers to a vegetable named *Plantago psyllium* and its derivatives, e.g., psyllium teguments.

As used herein, a "native wheat gluten" refers to a non-modified carbohydrate ingredient originating from wheat.

As conventionally admitted, a pet dry food is the final product of a process comprising an extrusion step followed by a drying step.

In certain embodiments, the nutritionally complete dry feline food according to the present disclosure has a moisture content of at most about 12%. In some embodiments, the said dry feline food has a moisture content of about 7% or less, such as about 5%. In certain non-limiting embodiments, the nutritionally complete dry feline food has a moisture content of more than about 3%. The examples illustrate a nutritionally complete dry feline food having a moisture content of about 5.5%. Specifically, a dry food composition can have less than about 10% moisture.

In certain embodiments, the dry food product has a kibble form. Non-limiting examples of kibbles include particulates, pellets, pieces of pet food, dehydrated meat, meat analog, vegetables, and combinations thereof and pet snacks, such as meat or vegetable jerky, rawhide, and biscuits.

The dry nutritionally complete feline food composition of the present disclosure can be manufactured by mixing together ingredients and kneading them to make consistent dough that can be cooked. The process of creating a dry pet food is usually done by baking and/or extruding. The dough is typically fed into a machine called an expander and/or extruder, which uses pressurized steam or hot water to cook the ingredients. While inside the extruder, the dough is under extreme pressure and high temperatures. The dough is then pushed through a die (specifically sized and shaped hole) and then cut off using a knife. The puffed dough pieces are made into kibble by passing it through a dryer so that moisture is dropped down to a defined target ensuring stability of the food until consumption. The kibble can then be sprayed with fats, oils, minerals, vitamins, the natural extracts cocktail and optionally sealed into packages.

In certain embodiments, the dry nutritionally complete feline food composition is packaged. In this way, the consumer is able to identify, from the packaging, the ingredients in the food product and confirm that it is suitable for the particular pet in question. In certain embodiments, the packaging can be metal, plastic, paper, or card.

Wet Food Composition

In certain embodiments, a nutritionally complete food composition as of the present disclosure is a wet food composition comprising (i) EPA/DHA in an amount of at least about 1.0 g/Mcal and (ii) Nitrogen Free Extract in an amount of no more than about 35 g/Mcal.

In certain embodiments, the nutritionally complete feline wet food composition comprises about 1.8 g/Mcal of EPA/DHA.

It is proposed that very high amounts of EPA/DHA, e.g., amounts of EPA/DHA higher than 10 g/Mcal can cause potential adverse effects, which can include hemostatic alterations due to anti-aggregatory effects on platelets, vitamin E deficiency, lipid peroxidation, and mild diarrhea.

In a particular embodiment, the amount of Nitrogen Free Extract present in a nutritionally complete feline wet food composition according to the present disclosure is about 32 g/Mcal.

In a particular embodiment, the amount of Nitrogen Free Extract present in a nutritionally complete feline wet food composition according to the present disclosure is at least about 1 g/Mcal.

Starch is one of the sources of the Nitrogen Free Extract comprised in a nutritionally complete feline wet food composition according to the present disclosure.

In certain particular embodiments, a nutritionally complete feline wet food composition according to the present disclosure comprises starch in an amount of no more than about 20 g/Mcal.

In certain embodiments, starch is provided from a cereal source. Certain non-limiting embodiments of sources of starch encompass staple foods like potatoes, wheat, maize (corn), rice, and cassava.

In certain embodiments, the nutritionally complete feline wet food composition comprises protein in an amount of at least about 117 g/Mcal.

In certain embodiments, the nutritionally complete feline wet food composition comprises protein in an amount of about 133 g/Mcal.

In certain embodiments, the nutritionally complete feline wet food composition comprises fat in an amount ranging from about 20 g/Mcal to about 45 g/Mcal.

In certain particular embodiments, the nutritionally complete feline dry food composition of the present disclosure comprises fat in an amount ranging from about 30 g/Mcal to about 45 g/Mcal, from about 35 to about 43 g/Mcal, from about 40 to about 42 g/Mcal, or from about 30 g/Mcal to about 40 g/Mcal. In certain embodiments, the nutritionally complete feline dry food composition of the present disclosure includes fat in an amount ranging from about 30 g/Mcal to about 35 g/Mcal.

Illustratively, in certain non-limiting embodiments, the wet food composition comprises fat in an amount of about 41 g/Mcal.

In an alternative embodiment, the nutritionally complete feline wet food composition comprises arginine in an amount of no more than about 9 g/Mcal.

In an illustrative embodiment, a nutritionally complete feline wet food composition comprises arginine in an amount of about 7.3 g/Mcal.

In certain embodiments, the nutritionally complete feline wet food composition comprises sodium ($Na^r$) in an amount of no more than about 0.7 g/Mcal. In certain embodiments, the nutritionally complete feline wet food composition of the present disclosure comprises sodium in an amount of about 0.60 g/Mcal.

In a particular embodiment, the nutritionally complete feline wet food composition of the present disclosure comprises about sodium in an amount of about 0.19 g/Mcal.

In certain embodiments, the nutritionally complete feline wet food composition comprises one or more components selected from the group consisting of psyllium and its derivatives, starch, protein of vegetable origin, and combinations thereof.

As an illustrative embodiment, the nutritionally complete feline wet food composition comprises at least (i) psyllium and its derivatives in an amount of at least about 0.1 g/Mcal, (ii) starch of cereal sources in an amount of no more than about 20 g/Mcal, and (iv) protein of vegetable origin in an amount of at least about 30 g/Mcal.

Protein of vegetable origin includes, without limitations, to protein from nuts, seeds, oleaginous fruits, *Spirulina, Chlorella*, klamath, soya, peanut, pumpkin seed, almond, beans, fenugreek, chickpeas, chia seeds, quinoa, buckwheat, oat bran, wheat, corn, potato, etc.

As conventionally admitted, a wet pet food is the final product of a process comprising a final step of sterilization (instead of a drying step).

In particular embodiments, the nutritionally complete wet feline food according to the present disclosure has a moisture content of more than about 30%. In some embodiments, the said wet feline food has a moisture content of about 40% or more. For Example, and not by the way of limitation, the examples provided herein illustrate a nutritionally complete wet feline food having a moisture content of 80%. Specifically, a wet food composition has more than 30% moisture.

In a particular embodiment, the wet food consists of a chunk form, more particularly of chunks in gravy form. In a particular embodiment, the wet food consists of chunks and gravy, chunks in jelly, loaf, mousse, terrine, or bite-form.

"Chunks and gravy" products comprise a preformed meat particle prepared by making a meat emulsion and by putting this meat emulsion through a muzzle under pressure and then cooked. A product, such as cooked meat, is diced into chunks, which are eventually mixed with a gravy or sauce. The two components are then filled into a container, usually a can or pouch, which is seamed or sealed and sterilized. As opposed to the ground loaf, chunk and gravy compositions have physically separated, discrete chunks (i.e., pieces of ground meat and grains) as prepared. These discrete particles are present in the gravy-type liquid in the final container. When serving, chunk and gravy products flow out of the can and can be easily mixed with other dry products. While the chunk and gravy products allow better integrity of the individual ingredients, the heterogeneous formulation of the chunk and gravy products are sometimes disfavored by consumers.

Wet food compositions are generally packaged in can-like containers and are considered "wet" in appearance because of the moisture contained therein. Two types of wet compositions are generally known in the art. The first is known in the art as "ground loaf" Loaf products are typically prepared by contacting a mixture of components under heat to produce an essentially homogeneous, intracellular honeycomb-type mass or "ground loaf" The ground loaf mass is then packaged into a cylindrical container, such as a can. Upon packing, ground loaf assumes the shape of the container such that the ground loaf must be cut when serving to a companion animal.

In certain embodiments, the dry nutritionally complete feline food composition is packaged. In this way, the consumer is able to identify, from the packaging, the ingredients in the food product and confirm that it is suitable for the particular pet in question. In certain embodiments, the packaging can be metal, plastic, paper or card.

Semi-Moist Food Composition

In alternative embodiments, a nutritionally complete food composition as described herein consists of a semi-moist food composition comprising (i) EPA/DHA in an amount of at least about 0.5 g/Mcal and (ii) Nitrogen Free Extract in an amount of no more than about 40 g/Mcal.

As conventionally admitted, a semi-moist pet food is the final product of a process allowing obtaining a moisture content value that is intermediate between a dry pet food and a wet pet food. In some embodiments, the said process can comprise a step of adding a humectant agent. In some embodiments, the said process comprises an extrusion step and a subsequent treatment step with Super-Heated Stream (SHS).

In some embodiments, the nutritionally complete semi-moist feline food according to the present disclosure containing more than about 12% and at most about 30% moisture. In an illustrative embodiment, a semi-moist food composition has from about 11% to about 20% moisture and/or a water activity of form about 0.64 to about 0.75.

In certain non-limiting embodiments, semi-moist food can be obtained using Super-Heated Stream (SHS) processes such as processes or methods described in the published patent applications WO2009/018990, WO2009/018996, WO2010/112097, WO2014/122072, WO2016/071372 and/or WO2016/071367.

In certain embodiments, the semi-moist food consists of soft semi-moist kibbles.

Use of the Nutritionally Complete Feline Food Composition

The present disclosure further provides for the use of a nutritionally complete feline food composition as described herein for preventing and/or treating cardiac hypertrophy, in particular for preventing or treating hypertrophic cardiomyopathy (HCM), including asymptomatic hypertrophic cardiomyopathy (aHCM) in feline animals, in particular cats.

In certain embodiments, the present disclosure relates to a nutritionally complete feline food composition comprising EPA/DHA and Nitrogen Free Extract, for its use for preventing and/or treating cardiac hypertrophy, wherein the nutritionally complete food composition consists of a dry food composition comprising EPA/DHA in an amount of at least about 0.5 g/Mcal, and Nitrogen Free Extract in an amount of no more than about 60 g/Mcal or the nutritionally complete food composition consists of a wet food composition comprising: EPA/DHA in an amount of at least about 1.0 g/Mcal and Nitrogen Free Extract in an amount of no more than about 35 g/Mcal.

As previously mentioned herein, cardiac hypertrophy is characterized by hypertrophy of the cardiac wall and more specifically of the left ventricle with thickening of the interventricular septum and left ventricular wall. It is known by the skilled person in the art that cardiac hypertrophy can be diagnosed by several ways. The cardiac hypertrophy can be diagnosed by echocardiographic measurement of maximum thickness of cardiac wall. Specifically, the maximum thickness of cardiac wall is measured in 3 areas in the interventricular septum in diastole (IVSd) and 2 areas in the left ventricular wall in diastole (LVWd).

Cardiac Troponin (cTnI) is a sensitive and specific marker of myocardial injury and increased in cats affected with asymptomatic hypertrophic cardiomyopathy (aHCM). Therefore, increasing of blood concentration of cardiac Troponin I is associated with time to cardiac death in cats. Further, blood concentration of Insulin like growth factor I (IGF-1) is also associated with cardiac measures of hypertrophy. Moreover, cardiac distensibility becomes abnormal (stiffening) with increased left-sided heart filling pressure, and dilation of the left atrium (LA-remodelling in response to the increased pressures). Cats without LA-remodeling are in the earliest stage of the HCM, i.e., aHCM. Cats with LA-remodeling are in a slight more advanced stage of aHCM, but are still in the early asymptomatic phase of aHCM.

As detailed elsewhere in the present specification, and as shown in the examples, the nutritionally complete feline food composition described herein acts positively on the various physiologic parameters associated with cardiac muscle alterations caused by a cardiac hypertrophy, especially HCM, including in an early stage thereof in the absence of visible symptoms (i.e., asymptomatic cardiac hypertrophy, encompassing asymptomatic HCM (aHCM).

Noticeably, the nutritionally complete feline food described herein has no effect on the inflammatory status by measurement of SAA of the treated feline, especially the treated cat.

Further, as shown in the examples herein, no undesirable effect was observed in feline animals fed with a nutritionally complete food as described herein, during a time period of one year or more.

Thus, a nutritionally complete feline food composition as described herein is useful for preventing or treating a cardiac hypertrophy, irrespective of the kind of causative physiological defect or causative physiological deregulation thereof. Illustratively, cardiac hypertrophy that can be prevented or treated by a nutritionally complete food composition according to the present disclosure can be subsequent to a blood pressure overload due to systemic hypertension or outflow obstruction, or alternatively can be subsequent to hormonal stimulation, as e.g., in hyperthyroidism or hypersomatotropism or acromegaly, or even caused by a specific genetic background of the feline animal, e.g., a specific genetic background of the cat.

In certain embodiments, the nutritionally complete feline food composition is used for decreasing thickening of cardiac wall.

In certain embodiments, the nutritionally complete feline food composition is used for decreasing blood concentration of Insulin like growth factor I (IGF-I).

In certain embodiments, the nutritionally complete feline food composition is used for decreasing blood concentration of cardiac Troponin I (cTnI).

In certain embodiments, the nutritionally complete feline food composition is used for regulating the heart rate.

The nutritionally complete feline food composition of the present disclosure is particularly useful for preventing and/or treating cats with cardiac hypertrophy. In a particular embodiment, said cats are affected with aHCM. In certain embodiments, said cats are affected with aHCM in absence of LA remodeling. In certain other embodiments, said cats are affected with aHCM in presence of LA remodeling.

Method of Treatment

The present disclosure also provides for a method for preventing and/or treating cardiac hypertrophy in a feline affected with aHCM. In certain embodiments, the method comprises at least a step of feeding said feline with a nutritionally complete feline composition as defined in the present disclosure.

As shown in the examples, a nutritionally complete feline food composition as described herein allows for prevention and/or treatment of a cardiac hypertrophy, irrespective of whether the said food composition is a dry food or a wet food. In certain embodiments, beneficial effects are obtained (i) in feline animals fed exclusively with the dry food described herein, (ii) in feline animals fed exclusively with the wet food described herein, as well as (iii) in feline animals fed with both the said dry food and the said wet food (i.e., “mixed dry/wet”).

In certain embodiments, the nutritionally complete feline food composition of the present disclosure is provided to feline animals, such as cats, on a daily basis.

In certain embodiments, a nutritionally complete feline food composition as disclosed herein can be provided to the feline animal to be treated as the sole nutritionally complete food during the time period of treatment. According to these embodiments, the said nutritionally complete feline food composition is provided to the animal on a daily basis during the time period of treatment.

In certain other embodiments, a nutritionally complete feline food composition as described herein can be provided to the feline animal to be treated in alternation with a second feline food composition. In certain embodiments, the second feline food composition is also a nutritionally complete feline food composition. The second nutritionally complete food composition can be selected from known feline food compositions, including the large variety of commercialized feline food compositions, such as any of the large variety of commercialized cat food compositions.

According to these other embodiments, the said nutritionally complete feline food composition is provided each alternate day, thus according to a time schedule of every two days. In another aspect of these other embodiments, the said nutritionally complete feline food composition is provided according to a time schedule of every three, four, five, six or seven days.

It shall be understood that, in the daily practice of feeding feline animals, especially cats, the animal owner can not proceed according to a systemic way of feeding the animal with a nutritionally complete feline food composition always on daily basis.

In certain embodiments, the beneficial effects of preventing or treating HCM, and especially of preventing or treating aHCM, is provided when the animal is fed with the nutritionally complete feline food composition described herein every alternate day. Feeding the animal every three, four, five, six or seven days will cause a reduced beneficial effect, which can require a longer time period of treatment.

Without wishing to be bound by any particular theory, an efficient prevention or treatment of a cardiac hypertrophy, such as a fully efficient prevention or treatment of an HCM, which includes a fully efficient treatment of an aHCM, requires that the feline animal, such as a cat, be provided with a nutritionally complete food composition as described herein on an alternate day basis, or on a daily basis.

The time period of feeding with a nutritionally complete feline food composition as described herein can range from several weeks to several years, depending notably on the severity of the cardiac hypertrophy.

As already specified elsewhere in the present description, cardiac hypertrophy can be caused by a systemic hypertension. In certain embodiments wherein the occurrence of a hypertensive state is a recent event and wherein cardiac hypertrophy is thus minimal (e.g., at a stage of aHCM), a short time period of treatment can be sufficient to restore a normal thickness of the cardiac wall, especially a normal thickness of the interventricular septum and/or of the left ventricular wall. In these embodiments, the animal can be simultaneously treated with an anti-hypertensive agent so as to prevent a novel occurrence of a cardiac hypertrophy, e.g., to prevent a novel occurrence of an HCM.

In certain other embodiments, the food regimen is provided to the animals to be treated during a longer period of time, such as during a period of time of 12 months or more, such as of 18 months of more, or such as 24 months or more, either (i) according to a feeding schedule comprising providing to the feline animal, such as a cat, exclusively the nutritionally complete feline food composition described herein or (ii) according to a schedule alternating the nutritionally complete feline food composition described herein and another feline food composition.

In certain embodiments, the feline animal is provided with a nutritionally complete feline food composition described herein for a longer period of time, such as two years or more. In certain embodiments, the feline animal is provided with a nutritionally complete feline food composition described herein for the whole lifetime of the said feline animal, such as a cat.

The present disclosure also includes a method for preventing or treating cardiac hypertrophy in a cat affected with aHCM comprising at least a step of making a feeding recommendation that includes a nutritionally complete feline composition as defined in the present disclosure.

The methods of the present disclosure do not affect kidney function in a cat affected with aHCM or HCM.

The methods of the present disclosure can further comprise a step of making a feeding recommendation that includes a nutritionally complete feline composition as defined in the present disclosure.

EXAMPLES

The presently disclosed subject matter will be better understood by reference to the following Examples, which are provided as exemplary of the disclosure, and not by way of limitation. The materials and methods used in the examples are summarized below.

Abbreviations 2d 2-dimensional
aHCM asymptomatic hypertrophic cardiomyopathy
DHA docosahexaenoic acid
EPA eicosapentaenoic acid
HCM hypertrophic cardiomyopathy
IVSd interventricular septum in diastole
LVWd left ventricular wall in diastole A. Materials and Methods A.1. Objective The purpose of this clinical trial was to investigate the effect of a novel high EPA/DHA and moderate Nitrogen Free Extract nutritionally complete feline food composition on the thickness of the cardiac walls for treatment of aHCM in cats.

A.2. Clinical Study

The control diets are named Dune (dry food formula) and Sloot (wet food formula).

The test diets are named Beach (dry formula) and Lake (wet formula).

Food compositions were given as dry only, wet only, or mixed dry/wet feeding according to cats' preferences.

Table 1 provides information of the cats that were included in the clinical study. A total of 44 cats were included in the clinical study, all diagnosed with aHCM. As shown in Table 2, 23 cats were fed the test food composition (Beach/Lake), and 21 cats were fed the control food composition (Dune/Sloot).

TABLE 1

| Population follow up study | |
|---|---|
| Total included cats | 44 (51 included, 7 did not complete 6 and/or 12 months point) |
| Sex | 13 F, 31 M |
| Breeds | BSH (3), DLH (4), DSH (27), ExSH, Maine Coon, Persian (2), Ragdoll cross (2), Selkirk Rex (3), Siamese (1) |
| BW (Body Weight) | Median 4.9 kg (2.9-8.7) |
| BCS (Body Condition Score) | Median 5 (3-9) |

TABLE 2

| Population distribution | | | | |
|---|---|---|---|---|
| | Food composition allocation | | | |
| | Total | Dry only | Wet only | Mixed Dry/Wet |
| Beach/Lake (test diet) | 23 | 11 | 2 | 10 |
| Dune/Sloot (control diet) | 21 | 4 | 0 | 17 |

Cats could choose per preference if they wanted to eat only dry, only wet or mixed dry/wet at the beginning of the study. They were given the diet for 12 months with an examination after 6 and 12 months (echocardiography, blood measures, BW, BCS).

The composition of the test dry food composition (BEACH), the control dry food composition (DUNE), the test wet food composition (LAKE) and of the control wet food composition (SLOOT) is described in Table 3.

The food composition is expressed in terms of energy density, more specifically in Metabolisable Energy (ME). Accordingly, the food composition in the present disclosure is expressed in weight per megacalories and has been determined by the formulae of the standard EN 16967:2017 E (European Standard EN 16967, Animal feeding stuffs: Methods of sampling and analysis—Predictive equations for metabolizable energy in feed materials and compound feed (pet food) for cats and dogs including dietetic food; July 2017).

The following parameters were measured:

- 2d-IVSd-max corresponding to the maximum thickness of the interventricular septum in diastole measured with 2D-mode.
- 2d-IVSd n areas ≥6 mm corresponding to the number of regions with at least 6 mm thickness of the interventricular septum in diastole measured with 2D-mode.
- 2d-IVSd sum of areas corresponding to the sum of thickness measured in the three separate regions of the interventricular septum in diastole measured with 2D-mode.
- 2d-LVWd-max corresponding to the maximum thickness of the left ventricular wall in diastole measured with 2D-mode.
- 2d-LVWd n areas ≥6 mm corresponding to the number of regions with at least 6 mm thickness of the left ventricular wall in diastole measured with 2D-mode.
- 2d-LVWD sum of areas corresponding to the sum of thickness measured in the two separate regions of the left ventricular wall in diastole measured with 2D-mode.
- 2d-IVSd and LVFW (n areas ≥6 mm) corresponding to the sum of thickness measured in the five separate regions of the interventricular septum in diastole and the left ventricular wall in diastole measured with 2D-mode.
- M-IVSd corresponding to the thickness of the interventricular septum in diastole measured by M-mode.
- M_LVFWd corresponding to the thickness of the left ventricular free wall in diastole measured by M-mode.
- LA_max_diameter corresponding to the maximum diameter of the left atrium.
- LA_max_diameter >16 corresponding to the maximum diameter greater than 16 mm of the left atrium.
- LA/Ao corresponding to the left atrical aortic root ratio.
- LA/Ao>1.5 corresponding to the left atrical aortic root ratio greater than 1.5.
- LA≥16 mm AND/OR LA/Ao≥1.5 n cases (0/1/2 criteria) corresponding to the number of cases with at least 16 mm of the diameter of the left atrium and/or to the left atrical aortic root ratio greater than 1.5.
- LVIDd corresponding to the left ventricular internal dimension in diastole.
- LVIDs corresponding to the left ventricular internal dimension in systole.
- Murmur grade corresponding to the heart sounds produced when blood flows across one of the heart valves.
- Murmur n cases grade: <3 or ≥3 corresponding to the number of cases with a murmur lower than 3 or with a murmur of at least 3.
- E/A Wave corresponding to the ratio of peak velocity blood flow from gravity in early diastole (E wave) to peak velocity flow in late diastole (A wave).
- Hearth rate corresponding to cat heart rate.

Max LVOT velocity corresponding to the left ventricular outflow tract.

Max RVOT velocity corresponding to the right ventricular outflow tract.

Insulin corresponding to the blood concentration of Insulin.

IGF-1 corresponding to the blood concentration of IGF-1.

SAA corresponding to the blood concentration of Serum Amyloid A.

NT-proBNP corresponding to the blood concentration of the N-terminal pro-B-type natriuretic peptide.

cTnI corresponding to the blood concentration of Troponin I, a marker of cardiac cell damage and indicative of developing heart failure and cardiac death.

Body Weight corresponding to the cat body weight.

BCS corresponding to the Body Condition Score of cats (BCS gives indications about cats' weight and health).

Serum concentration of creatinine corresponding to the creatine level in the blood.

Serum concentration of Blood urea nitrogen (BUN) corresponding to the level of nitrogen in the blood which comes from the waste product urea.

Serum concentration of Phosphate corresponding to the level of phosphate in the blood.

Serum concentration of Serum Fibroblastic growth factor-23 (FGF-23) corresponding to the level of FGF-23 in the blood.

The thickness of the heart is measured in 3 areas in the interventricular septum and 2 areas in the left ventricular free wall, using either 2d- or M-mode ultrasound technique.

The parameters serum concentration of creatinine, BUN, phosphate and FGF-23 allow to measure renal excretory function.

A.3. Methods Used for Measuring Different Parameters

Echocardiography (2D-, M-mode, and color flow, spectral and tissue Doppler) was performed on conscious cats without chemical restraint. Right parasternal 4 and 5 chamber long- and short-axis views at different levels (papillary muscle, mitral valve and aortic valve) were obtained. In addition, mainly for spectral Doppler of mitral inflow, pulmonary venous flow, left ventricular outflow (LVOT) and aortic flow, the left apical 4- and 5-chamber views were obtained.

The cranial right and left parasternal views optimizing the right ventricular outflow (RVOT) tract and pulmonary artery were obtained for spectral Doppler from these regions; measurements were made from the images which best optimized RVOT/PA flow.

Left ventricular, mitral valve and left atrial/aortic M-modes were obtained following cursor placement on the 2D images. M-mode measurements used leading-edge to leading-edge method.

2D measurements of the interventricular septum, the left ventricular cavity and left ventricular free wall at end of diastole and systole were made on the short-axis view at papillary muscle level, using blood-endocardial interface and myocardial-epicardial interface to guide cursor placement.

The 2D left atrial and aortic dimensions were obtained in the right parasternal short-axis view in diastole.

The 2D interventricular septum and left ventricular free wall measurements were obtained in the right parasternal short- and long-axis (4 or 5 chambers) view of the left ventricle in end-diastole (Freeman, Rush et al. 2014).

IVSd was measured in basal, mid and apical regions, and LVWd was measured in basal and mid regions from right parasternal long axis 4 or 5 chamber views, whichever optimized any focal hypertrophy. The measurements were noted as maximum thickness measured (max-), the sum of thicknesses measured in the five separate regions (sum-), and the number of regions with ≥6 mm thickness (n-).

For spectral Doppler measurements, for pulsed wave (or continuous wave if aliasing was evident), the following velocities were recorded: Mitral inflow E and A wave velocities, provided separated sufficiently, left ventricular outflow, aortic, right ventricular outflow and pulmonic velocities.

For pulmonary venous flow, the peak systolic and diastolic forward wave and atrial reversal wave velocities were recorded. The duration of the atrial reversal wave was compared with the mitral A wave duration. With sample volume in the left ventricular outflow tract enabling recording of both left ventricular outflow and mitral inflow, pulsed wave Doppler allowed the time from aortic valve closure to mitral E wave onset (the isovolumic relaxation time; IVRT) to be measured.

Colour M-mode was used in the left ventricle, on the left apical 4 chamber view, to assess mitral inflow, with M-mode cursor aligned with the column of mitral inflow. The Nyquist limit was reduced until the core of mitral inflow (E) was aliased, and colour M-mode obtained.

Without colour variance, the red-blue interface of the early mitral inflow wave was used to measure slope, to obtain the mitral flow propagation velocity (Schober, Fuentes et al. 2003).

From left apical 4 chamber views, aligning in turn with the longitudinal motion of the IVS, LVFW (and RVFW), with the sample volume placed in myocardium at the level of the atrioventricular annulus, PW-TDI spectra were obtained, and peak S', E' and A' velocities were measured.

General hypertrophy was defined as thickness ≥6 mm in all regions of both IVSd and LVWd.

Left atrial enlargement was defined as LA max≥16 mm (Schober and Maerz 2006) and/or LAmax/Ao≥1.5 mm (Abbott and MacLean 2006).

HCM was diagnosed when the thickest end-diastolic interventricular septum (IVSd) or left ventricular free wall (LVWd) segment or both on M- or 2D-mode measured >6 mm (Fox, Liu et al. 1995), with possible concurrent findings indicative of HCM like systolic anterior motion of the mitral valve, left atrial enlargement, or increased aortic velocity.

The blood concentration of Tropinin I and IGF-1 were analyzed by a CLIA Method using the Advia Centaur XP, with the kit of Siemens with the reference: Siemens, ADVIA Centaur TnI-Ultra® Assay (5 ReadyPack®-Testreagenzpackungen mit ADVIA Centaur® TnI-Ultra™ Binary Lite-Reagenz), 02790309 and the Immulite 2000/XPI.

Serum concentration of creatinine was measured according to the Kinetic colorimetric assay (Jaffe without deproteination) with the AU480 Chemistry Analyzer (Beckman Coulter).

Serum concentration of Blood urea nitrogen (BUN) was measured according to the Kinetic UV Test with the AU480 Chemistry Analyzer (Beckman Coulter).

Serum concentration of Phosphate was measured according to the photometric UV assay (Ammonium-phosphomolybdate-complex, UV-Test) with the AU480 Chemistry Analyzer (Beckman Coulter).

Serum concentration of Serum Fibroblastic growth factor-23 was measured using a two-step sandwich enzyme-linked immunosorbent assay (ELISA) with the FGF23 ELISA kit (Kainos Laboratories, Inc.)

A.4. Food Compositions Tested

Table 3 provides components and amounts thereof included in the food composition that were tested.

TABLE 3

Compositions tested

| | CONTROL FOOD | | | | TEST FOOD | | | |
|---|---|---|---|---|---|---|---|---|
| | % DM | | g/MCAL | | % DM | | g/MCal | |
| | DUNE dry | SLOOT wet | DUNE dry | SLOOT wet | BEACH dry | LAKE wet | BEACH dry | LAKE wet |
| NFE | 44.6 | 25 | 117.9 | 59.5 | 21.1 | 13.25 | 57.3 | 32.2 |
| Starch | 42 | 19.5 | 113.4 | 46.5 | 15.8 | 8 | 38.8 | 19.4 |
| Prot | 26.9 | 47.6 | 63.6 | 113.4 | 48.3 | 55 | 125 | 133.6 |
| EPA/DHA | 0.07 | 0.02 | 0.019 | 0.05 | 0.24 | 0.75 | 0.6 | 1.8 |
| fat | 15.5 | 16.2 | 36.8 | 38.5 | 15 | 17 | 34.8 | 41.3 |
| arginine | 1.28 | 2.62 | 3.2 | 6.2 | 2.28 | 3 | 7.8 | 7.3 |
| Na | 0.25 | 0.24 | 0.64 | 0.6 | 0.27 | 0.25 | 0.68 | 0.6 |
| Other nutrients | 11.4 | 8.32 | ND | ND | 12.81 | 10.75 | ND | ND |
| Total | 100 | 100 | NR | NR | 100 | 100 | NR | NR |
| ME (kcal/kg) | | | 3955 | 392 | | | 3765 | 383 |

"% DM": Weight percent, based on the total weight of dry matter of the food composition
"g/Mcal": Metabolizable energy density, as expressed as g/Mcal
"NFE" : Nitrogen Free Extract
"Starch": starch contained in the starting (raw) materials used for manufacturing the food compositions. The starch content is comprised in the NFE content of the food compositions.
"Other nutrients" comprise notably vitamins and minerals.
"ND": Not Disclosed
"NR": Not Relevant

Example 1: A Nutritionally Complete Food Composition Decreases Thickening of Cardiac Wall in Cats Affected with aHCM

1.1. Nutritionally Complete Feline Food Provided as a Dry Food, Wet Food and Mixed Dry/Wet Food Mean values of thickening interventricular septum and left ventricular wall and blood analysis (IGF-1 and Troponin I) in the test population (Beach/Lake) and fed all feeding types (dry, wet, mixed dry/wet), measured in months 0, 6 and 12, are shown in Table 4.

TABLE 4

Mean values (all feeding types combined: dry, wet, mixed dry/wet)

| Parameter | 0 months (start) | 6 months of test diet | 12 months of test diet |
|---|---|---|---|
| 2d-IVSd-max (mm) | 6.8857 | 6.6361 | 6.3448 |
| 2d-IVSd n areas ≥ 6 mm | 2 | 1.6522 | 1 |
| 2d-IVSd sum of areas (mm) | 18.6726 | 17.6187 | 16.7043 |
| 2d-LVWd-max (mm) | 6.1043 | 5.5557 | 5.5383 |
| 2d-LVWd n areas ≥ 6 mm | 0.913 | 0.3913 | 0.6957 |
| 2d-LVWd sum of areas (mm) | 11.6957 | 10.657 | 10.6461 |

TABLE 4-continued

Mean values (all feeding types combined: dry, wet, mixed dry/wet)

| Parameter | 0 months (start) | 6 months of test diet | 12 months of test diet |
|---|---|---|---|
| 2d-IVSd and LVFW (n areas ≥ 6 mm) | 2.913 | 2.0435 | 1.6957 |
| IGF-1 (ng/mL) | 473.17 | 391.43 | 384.62 |
| cTnI (ng/mL) | 0.6348 | 0.133 | 0.1622 |

The results depicted in Table 4 show that the nutritionally complete feline food causes a decrease in the thickness of the cardiac wall, especially in the interventricular septum and in the left ventricular wall of cats affected with an aHCM.

1.2. Nutritionally Complete Feline Food Provided Both as a Dry and a Wet Food (Mixed Dry/Wet)

Mean values of thickening interventricular septum and left ventricular wall and blood analysis (IGF-1 and Troponin I) in the test population (Beach/Lake) and fed only the mixed dry/wet composition, measured in months 0, 6 and 12, are shown in Table 5 hereunder.

TABLE 5

| Mean values (mixed dry/wet only) | | | |
|---|---|---|---|
| Parameter | 0 months (start) | 6 months of test diet | 12 months of test diet |
| 2d-IVSd-max (mm) | 6.89 | 6.57 | 6.47 |
| 2d-IVSd n areas ≥ 6 mm | 1.7 | 1.5 | 1.2 |
| 2d-IVSd sum of areas (mm) | 18.14 | 17.38 | 17.39 |
| 2d-LVWd-max (mm) | 6 | 5.39 | 5.67 |
| 2d-LVWd n areas ≥ 6 mm | 1.10 | 0.2 | 0.7 |
| 2d-LVWd sum of areas (mm) | 11.71 | 10.2 | 10.85 |
| 2d-IVSd and LVFW (n areas ≥ 6 mm) | 2.8 | 1.7 | 1.9 |
| IGF-1 (ng/mL) | 453.4 | 380.4 | 394.5 |
| cTnI (ng/mL) | 0.229 | 0.149 | 0.19 |

The results depicted in Table 5 show that the nutritionally complete feline food, freely provided as both a wet food and a dry food, causes a decrease in the thickness of the cardiac wall, especially in the interventricular septum and in the left ventricular wall of cats affected with an aHCM.

1.3. Nutritionally Complete Feline Food Provided as a Dry Food

Mean values of thickening interventricular septum and left ventricular wall and blood analysis (IGF-1 and Troponin I) in the test population (Beach/Lake) and fed only the dry composition, measured in months 0, 6 and 12, are shown in Table 6 hereunder.

TABLE 6

| Mean values (dry only) | | | |
|---|---|---|---|
| Parameter | 0 months (start) | 6 months of test diet | 12 months of test diet |
| 2d-IVSd-max (mm) | 6.91 | 6.73 | 6.32 |
| 2d-IVSd n areas ≥ 6 mm | 2.27 | 1.91 | 1 |
| 2d-IVSd sum of areas (mm) | 19.19 | 17.96 | 16.3 |
| 2d-LVWd-max (mm) | 6.2 | 5.89 | 5.56 |
| 2d-LVWd n areas ≥ 6 mm | 0.73 | 0.64 | 0.82 |
| 2d-LVWd sum of areas (mm) | 11.61 | 11.46 | 10.74 |
| 2d-IVSd and LVFW (n areas ≥ 6 mm) | 3 | 2.55 | 1.82 |

TABLE 6-continued

| Mean values (dry only) | | | |
|---|---|---|---|
| Parameter | 0 months (start) | 6 months of test diet | 12 months of test diet |
| IGF-1 (ng/mL) | 522.6 | 416.6 | 346.0 |
| cTnI (ng/mL) | 1.10 | 0.16 | 0.16 |

The results depicted in Table 6 show that the nutritionally complete feline food, freely provided as a dry food, causes a decrease in the thickness of the cardiac wall, especially in the interventricular septum and in the left ventricular wall of cats affected with an aHCM.

1.4. Nutritionally Complete Feline Food Provided as a Wet Food

Mean values of thickening interventricular septum and left ventricular wall and blood analysis (IGF-1 and Troponin I) in the test population (Beach/Lake) and fed only the wet composition, measured in months 0, 6 and 12, are shown in Table 7 hereunder.

TABLE 7

| Mean values (wet only) | | | |
|---|---|---|---|
| Parameter | 0 months (start) | 6 months of test diet | 12 months of test diet |
| 2d-IVSd-max (mm) | 6.75 | 6.45 | 5.85 |
| 2d-IVSd n areas ≥ 6 mm | 2 | 1 | 0 |
| 2d-IVSd sum of areas (mm) | 18.5 | 16.95 | 15.5 |
| 2d-LVWd-max (mm) | 6.1 | 4.55 | 4.75 |
| 2d-LVWd n areas ≥ 6 mm | 1 | 0 | 0 |
| 2d-LVWd sum of areas (mm) | 12.10 | 8.55 | 9.1 |
| 2d-IVSd and LVFW (n areas ≥ 6 mm) | 3 | 1 | 0 |
| IGF-1 (ng/mL) | 300 | 308 | 357.5 |
| cTnI (ng/mL) | 0.12 | 0.06 | 0.07 |

The results depicted in Table 7 show that the nutritionally complete feline food, freely provided as a wet food, causes a decrease in the thickness of the cardiac wall, especially in the interventricular septum and in the left ventricular wall of cats affected with an aHCM.

1.5. P Values of Food Composition Effects

P values of food composition effects in the whole population of cats affected with aHCM are shown in Table 8 hereunder.

TABLE 8

| Overall population. P values of effects (Bold values are significant P < 0.05) | | | | | | | | |
|---|---|---|---|---|---|---|---|---|
| | Fixed Effects | | | | | | | |
| | | | Diet* | Slice Diet | | Slice Time | | |
| Parameter | Diet | Time | Time | Beach | Dune | M00 | M06 | M12 |
| 2d-IVSd-max | 0.0477 | **0.0039** | 0.4757 | 0.0105 | 0.1426 | 0.1132 | 0.1716 | 0.0219 |
| 2d-IVSd n areas ≥6 mm | 0.2347 | **0.0001** | 0.1994 | **0.0001** | 0.1259 | 1 | 0.3253 | 0.0631 |

TABLE 8-continued

Overall population. P values of effects (Bold values are significant P < 0.05)

| | Fixed Effects | | | Slice Diet | | Slice Time | | |
|---|---|---|---|---|---|---|---|---|
| Parameter | Diet | Time | Diet* Time | Beach | Dune | M00 | M06 | M12 |
| 2d-IVSd sum of areas | 0.1279 | **0.0001** | 0.4646 | **0.0001** | 0.0224 | 0.3721 | 0.2034 | 0.0612 |
| 2d-LVWd-max | 0.1411 | **0.0035** | 0.2845 | **0.002** | 0.4198 | 0.5414 | 0.1132 | 0.0812 |
| 2d-LVWd n areas ≥6 mm | 0.1151 | 0.0661 | 0.4169 | 0.0349 | 0.7633 | 0.0927 | 0.2688 | 0.9484 |
| 2d-LVWd sum of areas | 0.1582 | 0.0109 | 0.3585 | **0.0064** | 0.519 | 0.5954 | 0.1262 | 0.1044 |
| 2d-IVSd and LVFW (n areas ≥6 mm) | 0.1013 | **0.0005** | 0.3088 | **0.0006** | 0.2137 | 0.6162 | 0.0973 | 0.0586 |
| IVSd and LVFW n = 5 (Y = general hypertrophy) | 0.154 | 0.0876 | 0.8647 | 0.4309 | 0.1336 | 0.1841 | 0.2226 | 0.6406 |
| M-IVSd | 0.8249 | 0.0338 | 0.4492 | 0.0232 | 0.5776 | 0.3105 | 0.7702 | 0.8144 |
| M_LVFWd | 0.7247 | **0.0001** | 0.6119 | **0.0001** | **0.0001** | 0.5193 | 0.6019 | 0.7292 |
| LA_max_diameter | 0.5041 | 0.166 | 0.6414 | 0.1445 | 0.689 | 0.3482 | 0.5038 | 0.9358 |
| LA_max_diameter ≥16 | 0.99 | 0.3614 | 0.6192 | 0.7723 | 0.3162 | 0.9578 | 0.5255 | 0.5621 |
| LA/Ao | 0.1436 | 0.1771 | 0.931 | 0.3541 | 0.4519 | 0.174 | 0.3351 | 0.2321 |
| LA/Ao >1.5 | 0.0487 | 0.1979 | 0.6015 | 0.2649 | 0.7026 | 0.2732 | 0.0783 | 0.3052 |
| LA ≥16 mm AND/OR LA/Ao ≥1.5 n cases (0/1/2 criteria) | 0.2987 | 0.4696 | 0.4696 | 0.4348 | 0.5039 | 0.5003 | 0.1269 | 0.75 |
| LVIDd | 0.3759 | 0.0343 | 0.4161 | 0.2965 | 0.0512 | 0.1935 | 0.8925 | 0.3869 |
| LVIDs | 0.2175 | 0.3509 | 0.6271 | 0.3464 | 0.5955 | 0.1907 | 0.2009 | 0.5940 |
| Murmur grade | 0.5685 | 0.505 | 0.1345 | 0.2761 | 0.2448 | 0.2035 | 0.5136 | 0.6543 |
| Murmur n cases grade: <3 or ≥3 | 0.589 | 0.8247 | 0.2119 | 0.1161 | 0.7134 | 0.1556 | 0.7583 | 0.7377 |
| E/A Wave | 0.0637 | **0.0028** | 0.2102 | **0.0074** | 0.8865 | 0.0732 | NA | 0.4701 |
| Hearth rate | 0.8295 | **0.0036** | 0.0318 | **0.0005** | 0.5498 | 0.2801 | NA | 0.1546 |
| Max LVOT velocity | 0.8975 | 0.0798 | 0.1518 | 0.0193 | 0.5762 | 0.5381 | 0.6624 | 0.5912 |
| Max RVOT velocity | 0.3027 | **0.0094** | 0.8174 | 0.1089 | 0.0648 | 0.3273 | 0.6894 | 0.3235 |
| Insulin | 0.0746 | 0.0495 | 0.5232 | 0.228 | 0.1139 | 0.1458 | 0.4844 | 0.0493 |
| IGF-1 | 0.2305 | 0.2115 | 0.0195 | **0.0046** | 0.7519 | 0.7896 | 0.0986 | 0.0768 |
| SAA | 0.0414 | 0.4115 | 0.5526 | 0.4771 | 0.5475 | 0.6223 | 0.1338 | 0.0776 |
| NT-proBNP | 0.5053 | 0.3336 | 0.8815 | 0.5825 | 0.5037 | 0.6233 | 0.5157 | 0.4486 |
| cTnI | 0.948 | **0.0012** | 0.0971 | **0.0004** | 0.2042 | 0.3828 | 0.6435 | 0.558 |
| Body Weight | 0.6741 | 0.1135 | 0.9246 | 0.2053 | 0.4813 | 0.6998 | 0.7118 | 0.6276 |
| BCS | 0.4678 | 0.4507 | 0.9065 | 0.5115 | 0.782 | 0.5464 | 0.4014 | 0.6013 |

For a better comprehension, “Fixed effect” is the influence of the food composition and time and interaction between food composition and time on the parameter tested. “Slice diet” is the comparison between time points within one food composition (test or control). P value is the risk of making a mistake by saying that the timepoints are significantly different, with p value corrected for 3 timepoints.

The results show that the food composition has proven to reverse thickening of the interventricular septum and left ventricular wall in diastole in cats with asymptomatic HCM (aHCM). The ‘mean number of thickened areas above the cut-off value of 6 mm’ decreases with 50% in the ‘3 areas of the interventricular septum’ and with 40% in the ‘5 areas of the interventricular septum and left ventricular wall together’. The ‘mean thickness of the left ventricular wall’ decreases to below cut-off value of 6 mm.

Moreover, the food composition has proven to significantly reduce IGF-1 blood levels as well as to significantly reduce blood levels of cardiac Troponin I (cTnI).

Further, the results show there is no significant change in the cat body weight and also in the BCS. Accordingly, the food composition is nutritionally complete.

Example 2: A Nutritionally Complete Food Composition Decreases Thickening of Cardiac Wall in Cats Affected with Asymptomatic HCM without Left Atrium Remodeling (LA-Remodeling)

P values of food composition effects in cats affected with asymptomatic HCM in presence of left atrium remodeling are shown in Table 9 hereunder.

TABLE 9

Presence of LA remodeling. P values of effects (Bold values are significant P < 0.05)

| | Fixed Effects | | | | | | | |
|---|---|---|---|---|---|---|---|---|
| | | | Diet* | Slice Diet | | Slice Time | | |
| Parameter | Diet | Time | Time | Beach | Dune | M00 | M06 | M12 |
| 2d-IVSd-max | 0.2665 | 0.504 | 0.5343 | 0.4538 | 0.5938 | 0.3057 | 0.6768 | 0.1608 |
| 2d-IVSd n areas ≥6 mm | 0.4249 | 0.0105 | 0.5104 | 0.014 | 0.362 | 0.827 | 0.6623 | 0.1944 |
| 2d-IVSd sum of areas | 0.4713 | **0.0079** | 0.8644 | **0.0034** | 0.1589 | 0.7027 | 0.5066 | 0.4046 |
| 2d-LVWd-max | 0.2022 | 0.257 | 0.9073 | 0.3567 | 0.6435 | 0.3739 | 0.199 | 0.2831 |
| 2d-LVWd n areas ≥6 mm | 0.2316 | 0.1471 | 0.5166 | 0.0785 | 0.7966 | 0.7539 | 0.0948 | 0.5406 |
| 2d-LVWd sum of areas | 0.2328 | 0.3203 | 0.9408 | 0.4222 | 0.7058 | 0.436 | 0.266 | 0.3062 |
| 2d-IVSd and LVFW (n areas ≥6 mm) | 0.2529 | 0.0951 | 0.9052 | 0.1789 | 0.4569 | 0.1774 | 0.3214 | 0.258 |
| M-IVSd | 0.9849 | 0.2037 | 0.8273 | 0.2479 | 0.6716 | 0.9575 | 0.6991 | 0.7093 |
| M_LVFWd | 0.2333 | **0.0001** | 0.8093 | **0.0001** | **0.0001** | 0.3665 | 0.2219 | 0.6438 |
| LA_max_diameter | 0.6706 | 0.6693 | 0.6652 | 0.9696 | 0.4944 | 0.472 | 0.8468 | 0.6236 |
| LA_max_diameter ≥16 | 0.8728 | 0.2918 | 0.87 | 0.4168 | 0.5699 | 0.9529 | 0.5889 | 0.9032 |
| LA/Ao | 0.1028 | 0.1671 | 0.5688 | 0.6993 | 0.1436 | 0.152 | 0.5141 | 0.0817 |
| LA ≥16 mm AND/OR LA/Ao ≥1.5 n cases (0/1/2 criteria) | 0.1516 | 0.1676 | 0.7044 | 0.16 | 0.7403 | 0.5223 | 0.1144 | 0.3387 |
| LVIDd | 0.8571 | 0.5128 | 0.4605 | 0.9472 | 0.2547 | 0.5737 | 0.7542 | 0.4942 |
| LVIDs | 0.2175 | 0.3509 | 0.6271 | 0.3464 | 0.5955 | 0.1907 | 0.2009 | 0.594 |
| Murmur grade | 0.5029 | 0.6881 | 0.6881 | 0.5723 | 0.8288 | 0.3076 | 0.7324 | 0.7324 |
| Murmur n cases grade: <3 or ≥3 | 0.4801 | 0.2267 | 0.9976 | 0.4674 | 0.4718 | 0.6153 | 0.5811 | 0.6427 |
| E/A Wave | 0.1073 | 0.1134 | 0.5319 | 0.1718 | 0.3975 | 0.0274 | | 0.584 |
| Hearth rate | 0.7282 | 0.4887 | 0.1177 | 0.106 | 0.5281 | 0.5643 | | 0.2438 |
| Max LVOT velocity | 0.6865 | 0.0371 | 0.1065 | 0.0127 | 0.3524 | 0.2177 | 0.9273 | 0.8159 |
| Max RVOT velocity | 0.8029 | 0.0145 | 0.8414 | 0.19 | 0.0558 | 0.5838 | 0.922 | 0.9379 |
| Insulin | 0.1782 | 0.4953 | 0.4039 | 0.2076 | 0.98 | 0.8414 | 0.1399 | 0.1517 |
| IGF-1 | 0.0188 | 0.5143 | 0.0567 | 0.045 | 0.6294 | 0.6504 | 0.032 | **0.0042** |
| SAA | 0.2589 | 0.4788 | 0.1511 | 0.2272 | 0.5017 | 0.4924 | 0.3852 | 0.0836 |
| NT-proBNP | 0.6933 | 0.1065 | 0.6941 | 0.4634 | 0.1558 | 0.874 | 0.7392 | 0.5305 |
| cTnI | 0.5743 | 0.0364 | 0.0618 | **0.0074** | 0.3328 | 0.1103 | 0.9324 | 0.8312 |
| Body Weight | 0.971 | 0.2303 | 0.8826 | 0.3017 | 0.6637 | 0.9214 | 0.9233 | 0.9289 |
| BCS | 0.5517 | 0.4621 | 0.687 | 0.9434 | 0.3402 | 0.5328 | 1 | 0.486 |

P values of food composition effects in cats affected with aHCM in absence of left atrium remodeling are shown in Table 10 hereunder.

TABLE 10

Absence of LA remodeling. P values of effects (Bold values are significant P < 0.05)

| | Fixed Effects | | | | | | | |
|---|---|---|---|---|---|---|---|---|
| | | | Diet* | Slice Diet | | Slice Time | | |
| Parameter | Diet | Time | Time | Beach | Dune | M00 | M06 | M12 |
| 2d-IVSd-max | 0.1178 | **0.0024** | 0.7588 | **0.0078** | 0.1306 | 0.2354 | 0.1681 | 0.0892 |
| 2d-IVSd n areas ≥6 mm | 0.39 | **0.0062** | 0.3845 | **0.0046** | 0.3562 | 0.886 | 0.3726 | 0.2016 |

TABLE 10-continued

Absence of LA remodeling. P values of effects (Bold values are significant P < 0.05)

| | Fixed Effects | | | | | | | | |
|---|---|---|---|---|---|---|---|---|---|
| | | | Diet* | Slice Diet | | Slice Time | | | |
| Parameter | Diet | Time | Time | Beach | Dune | M00 | M06 | M12 |
| 2d-IVSd sum of areas | 0.1851 | **0.0012** | 0.5191 | **0.0024** | 0.1435 | 0.4026 | 0.2943 | 0.0955 |
| 2d-LVWd-max | 0.4293 | **0.0077** | 0.1321 | **0.0015** | 0.5609 | 0.9002 | 0.37 | 0.175 |
| 2d-LVWd n areas ≥6 mm | 0.2206 | 0.4181 | 0.5504 | 0.2606 | 0.9179 | 0.8231 | 0.3166 | 0.1656 |
| 2d-LVWd sum of areas | 0.43 | 0.0207 | 0.1971 | **0.0044** | 0.7517 | 0.8739 | 0.3155 | 0.219 |
| 2d-IVSd and LVFW (n areas ≥6 mm) | 0.2823 | **0.007** | 0.2809 | **0.003** | 0.4791 | 0.9803 | 0.2124 | 0.1573 |
| M-IVSd | 0.7419 | 0.0349 | 0.2038 | **0.0073** | 0.8029 | 0.187 | 0.9919 | 0.585 |
| M_LVFWd | 0.4212 | **0.0001** | 0.159 | **0.0001** | **0.0001** | 0.9521 | 0.9922 | 0.0648 |
| LA_max_diameter | 0.3608 | **0.0022** | 0.1161 | **0.0023** | 0.0835 | 0.2816 | 0.1137 | 0.652 |
| LA/Ao | 0.8276 | 0.4274 | 0.4919 | 0.4706 | 0.4369 | 0.7917 | 0.4276 | 0.5579 |
| LVIDd | 0.1042 | 0.049 | 0.3357 | 0.1632 | 0.1007 | 0.1536 | 0.8804 | 0.0618 |
| LVIDs | 0.1771 | 0.7878 | 0.4078 | 0.5969 | 0.5324 | 0.7215 | 0.3942 | 0.0686 |
| Murmur grade | 0.8516 | 0.7003 | 0.0466 | 0.2229 | 0.1398 | 0.4035 | 0.4937 | 0.3063 |
| Murmur n cases grade: <3 or ≥3 | 0.7301 | 0.8078 | 0.0523 | 0.1533 | 0.267 | 0.1603 | 0.2696 | 0.2748 |
| Hearth rate | 0.9901 | **0.0009** | 0.0901 | **0.0007** | 0.1412 | 0.3346 | | 0.3447 |
| Max LVOT velocity | 0.6532 | 0.8795 | 0.761 | 0.6541 | 0.9875 | 0.8425 | 0.527 | 0.6636 |
| Max RVOT velocity | 0.2637 | 0.2297 | 0.731 | 0.2288 | 0.6615 | 0.4551 | 0.6189 | 0.1827 |
| Insulin | 0.2502 | 0.0601 | 0.1395 | 0.6868 | 0.0177 | 0.0877 | 0.7334 | 0.1854 |
| IGF-1 | 0.6789 | 0.3282 | 0.1778 | 0.0635 | 0.7866 | 0.3501 | 0.8914 | 0.7109 |
| SAA | 0.0852 | 0.7246 | 0.7246 | 0.756 | 0.7531 | 0.1448 | 0.2635 | 0.5609 |
| NT-proBNP | 0.8172 | 0.89 | 0.9699 | 0.9729 | 0.8941 | 0.7668 | 0.8394 | 0.8798 |
| cTnI | 0.5968 | 0.0341 | 0.842 | 0.0619 | 0.3605 | 0.7919 | 0.5031 | 0.6058 |
| Body Weight | 0.6403 | 0.4996 | 0.9974 | 0.664 | 0.7389 | 0.6412 | 0.6516 | 0.6593 |
| BCS | 0.5891 | 0.587 | 0.2175 | 0.3923 | 0.327 | 0.7364 | 0.28 | 0.914 |

The results show that the food composition has also proven to reverse thickening of the interventricular septum and left ventricular wall in diastole in cats with aHCM in absence of LA remodeling. Indeed, cats without LA remodeling showed the same results as the complete population, while cats with LA remodeling only showed effect on mean number of thickened areas above cut-off value of 6 mm in the 3 areas of interventricular septum (2d-IVSd n areas ≥6 mm) and the sum of thickness values measured in the three separate regions of the interventricular septum in diastole measured with 2D-mode (2d-IVSd sum), but not in the 5 areas of the interventricular septum and left ventricular wall together (2d-IVSd and LVFW n areas ≥6 mm), nor on the mean thickness of the left ventricular wall (2d-LVWd-max). The reduction of cTnI is present in cats with and without LA remodeling. This can be explained by cats without LA remodeling being in the earliest stages of disease without stiffening of the heart and are still susceptible to the diet effect.

Example 3: A Nutritionally Complete Feline Food Composition does not Affect Kidney Function in Cats with aHCM It was surprisingly found that a high amount of protein, i.e., dry food composition comprising protein in an amount of at least 115 g/Mcal and wet food composition comprising protein in an amount of at least 117 g/Mcal, does not have deleterious effects on renal function in cats affected with aHCM.

Serum concentrations of creatinine, BUN, phosphate, and fibroblastic growth factor-23 (FGF-23) were measured in non-sedated, fasted cats before and after 6 and 12 months of feeding the allocated food compositions (Table 11).

One-Sample Wilcoxon signed rank test analyzed whether serum concentrations were below upper laboratory reference range at baseline. Two-way repeated measures ANOVA compared the measured variables with both time (baseline, 6 and 12 months) and control and test groups with a significance level of 5%. Results are expressed as median (range).

Serum concentrations of the 4 parameters were significantly below upper laboratory reference range at baseline (P<0.0001). There was a significant diet-time interaction for BUN (Blood Urea Nitrogen) (P=0.0013) with significant increase after 6 and 12 months of feeding the test food composition, but no significant change over time for creatinine, phosphate or FGF-23 in either group, and the small number of cats with serum concentration upper than reference range at each timepoint.

The results in Table 11 show that:

For creatinine, there is only a significant difference between test 12 months and control 0 months, and test 12 months and control 12 months. However, there is no difference over time in test group and in control group.

For BUN: there is only a significant difference between test 0 months and test 6 months, and test 0 months and test 12 months. However, there is no difference over time in control group, and no difference between test group and control group on separate timepoints.

For phosphate: there is only a significant difference between test 0 months and test 6 months, and test 0 months and test 12 months. However, there is no difference over time in control group, and no difference between test group and control group on separate timepoints.

For FGF23: there is only a significant difference between test 12 months and control 6 months. However, there is no change over time within test group or within control group. There is no difference between other timepoints of test group and other timepoints of control group.

TABLE 11

Results for serum creatinine, BUN, phosphate, and FGF-23 concentrations

| Time | Test food | | | Control food | | |
|---|---|---|---|---|---|---|
| (months) | 0 | 6 | 12 | 0 | 6 | 12 |
| Creatinine (□ mol/L) | 120 (96-164)$^{ab}$ [0 of 23] | 113 (72-204)$^{ab}$ [1 of 23] | 111 (65-167)$^{a}$ [0 of 23] | 127 (95-180)$^{b}$ [3 of 21] | 127 (82-167)$^{ab}$ [0 of 21] | 119 (80-221)$^{b}$ [3 of 21] |
| BUN (mmol/L) | 8.9 (6.6-16.1)$^{a}$ [1 of 23] | 10. (7.3-13.4)$^{b}$ [0 of 23] | 10.3 (7.0-13.1)$^{b}$ [0 of 23] | 9.5 (7.3-22.5)$^{ab}$ [1 of 21] | 8.9 (7.1-14.1)$^{ab}$ [1 of 21] | 9.3 (7.7-1.97)$^{ab}$ [5 of 21] |
| Phosphate (mmol/L) | 1.3 (0.7-2.2)$^{a}$ [1 of 23] | 1.3 (1.1-1.7)$^{b}$ [0 of 23] | 1.3 (0.9-1.5)$^{b}$ [0 of 23] | 1.3 (0.7-2)$^{ab}$ [0 of 21] | 1.3 (0.9-1 .6)$^{ab}$ [0 of 21] | 1.3 (0.8-1.8)$^{ab}$ [0 of 21] |
| FGF-23 (pg/mL) | 89.3 (21.0-3043.1)$^{ab}$ [1 of 23] | 73.7 (4.5-2358.1)$^{ab}$ [1 of 23] | 76.11 (43.8-4263.6)$^{a}$ [1 of 23] | 119 (12.7-741.6)$^{ab}$ [1 of 21] | 158.9 (40.1-656.4)$^{b}$ [0 of 21] | 113.8 (49.4-1520.8)$^{ab}$ [2 of 21] |

Different superscript letters ("a", "b" and "ab") identifying significant within- and between-group comparison differences for different time points with square brackets indicating number of cats with serum concentrations ≥upper reference range «(x-x)»: (minimum range-maximum range)

"b" is significantly different from "a"

"ab" is not significant

Therefore, there is no detrimental effects of feeding a nutritionally complete food composition comprising a high amount of protein over 12 months on kidney function in cats with aHCM.

Although the presently disclosed subject matter and its advantages have been described in detail, it should be understood that various changes, substitutions and alterations can be made herein without departing from the spirit and scope of the application as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, means, methods, or steps.

For any patents, patent applications, publications, product descriptions, and protocols are cited throughout this application, the disclosures of all of which are incorporated herein by reference in their entireties for all purposes.

REFERENCES

Abbott, J. A. and H. N. MacLean (2006). "Two-dimensional echocardiographic assessment of the feline left atrium." J Vet Intern Med 20(1): 111-119.

Freeman, L. M., J. E. Rush, S. M. Cunningham and B. J. Bulmer (2014). "A randomized study assessing the effect of diet in cats with hypertrophic cardiomyopathy." J Vet Intern Med 28(3): 847-856.

Fox, P. R., S. K. Liu and B. J. Maron (1995). "Echocardiographic assessment of spontaneously occurring feline hypertrophic cardiomyopathy. An animal model of human disease." Circulation 92(9): 2645-2651.

Fox P R, Keene B W et al. International collaborative study to assess cardiovascular risk and evaluate long-term health in cats with preclinical hypertrophic cardiomyopathy and apparently healthy cats: The REVEAL Study. Journal of Veterinary Internal Medicine: April. 2018; 32(3):930-943.

Riesen S C, Kovacevic A, Lombard C W, et al. Prevalence of heart disease in symptomatic cats: an overview from 1998 to 2005. Schweizer Archiv fur Tierheilkunde 2007; 149:65-71.

Rush J E. Therapy of feline hypertrophic cardiomyopathy (1998). Veterinary Clinics of North America: Small Animal Practice; 28:1459-1479

Schober, K. E., V. L. Fuentes and J. D. Bonagura (2003). "Comparison between invasive hemodynamic measurements and noninvasive assessment of left ventricular diastolic function by use of Doppler echocardiography in healthy anesthetized cats." Am J Vet Res 64(1): 93-103.

Schober, K. E. and I. Maerz (2006). "Assessment of left atrial appendage flow velocity and its relation to spontaneous echocardiographic contrast in 89 cats with myocardial disease." J Vet Intern Med 20(1): 120-130.

The invention claimed is:

1. A nutritionally complete feline food composition comprising:

a) eicosapentaenoic acid/docosahexaenoic acid (EPA/DHA) in an amount of at least about 0.5 g/Mcal, b) Nitrogen Free Extract in an amount of no more than about 60 g/Mcal, c) starch in an amount of no more than about 40 g/Mcal, and d) protein in an amount of at least about 115 g/Mcal;

e) one or more components selected from the group consisting of i) barley in an amount of at least about 45 g/Mcal, ii) psyllium and its derivatives in an amount of at least about 3.50 g/Mcal, iii) native wheat gluten in an amount of at least about 50 g/Mcal, and iv) combinations thereof;

f) fat in an amount of from about 20 g/Mcal to about 45 g/Mcal; and g) sodium in an amount of from about 0.19 g/Mcal to about 0.70 g/Mcal, wherein the nutritionally complete feline food composition is a dry food composition.

2. The nutritionally complete feline food composition of claim 1, wherein the dry food composition comprises arginine in an amount of no more than about 9 g/Mcal.

3. A method for treating cardiac hypertrophy in a feline in need thereof, the method comprising providing the feline the composition according to claim 1.

4. The method of claim 3, wherein the feline is a cat.

5. The method of claim 4, wherein the cat is affected with asymptomatic hypertrophic cardiomyopathy.

6. The nutritionally complete feline food composition of claim 1, wherein the nutritionally complete feline food composition comprises fat in an amount of from about 30 g/Mcal to about 40 g/Mcal.

7. The nutritionally complete feline food composition of claim 6, wherein the nutritionally complete feline food composition comprises fat in an amount of from about 30 g/Mcal to about 35 g/Mcal.

8. The nutritionally complete feline food composition of claim 1, wherein the nutritionally complete feline food composition comprises protein in an amount of about 125 g/Mcal.

9. The nutritionally complete feline food composition of claim 1, wherein the nutritionally complete feline food composition comprises EPA/DHA in an amount of about 0.6 g/Mcal.

10. The nutritionally complete feline food composition of claim 1, wherein the nutritionally complete feline food composition comprises sodium in an amount of about 0.68 g/Mcal.

11. The nutritionally complete feline food composition of claim 1, wherein the dry food composition has a kibble form.

12. The nutritionally complete feline food composition of claim 2, wherein the dry food composition comprises arginine in an amount of no more than about 8 g/Mcal.

* * * * *